US009782401B1

(12) United States Patent
Jiang et al.

(10) Patent No.: US 9,782,401 B1
(45) Date of Patent: Oct. 10, 2017

(54) **METHOD OF ISOLATING PHENANTHROINDOLIZIDINE ALKALOIDS FROM *TYLOPHORA ATROFOLLICULATA* WITH HIF-1 INHIBITORY ACTIVITY, COMPOSITIONS COMPRISING THEM AND THEIR USE**

(71) Applicant: Macau University of Science and Technology, Taipa (MO)

(72) Inventors: Zhi-Hong Jiang, Taipa (MO); Jing-Rong Wang, Taipa (MO); Cheng-Yu Chen, Taipa (MO); Guo-Yuan Zhu, Taipa (MO)

(73) Assignee: Macau University of Science and Technology (MO)

( * ) Notice: Subject to any disclaimer, the term of this patent is extended or adjusted under 35 U.S.C. 154(b) by 0 days.

(21) Appl. No.: 15/142,373

(22) Filed: Apr. 29, 2016

(51) Int. Cl.
*A61K 36/24* (2006.01)
*A61K 31/4745* (2006.01)

(52) U.S. Cl.
CPC .......... *A61K 31/4745* (2013.01); *A61K 36/24* (2013.01)

(58) Field of Classification Search
USPC ........................................ 514/283, 250, 339
See application file for complete search history.

(56) References Cited

U.S. PATENT DOCUMENTS 7,332,502 B2 * 2/2008 Lee ..................... C07D 471/04
514/283

OTHER PUBLICATIONS

J. M. Brown, "The Hypoxic Cell: A Target for Selective Cancer Therapy-Eighteenth Bruce F. Cain Memorial Award Lecture", Cancer Research, vol. 59, pp. 5863-5870, 1999.
D. G. Nagle and Y. D. Zhou, "Natural Product-Based Inhibitors of Hypoxia-Inducible Factor-1 (HIF-1)", Cur. Drug Targets, vol. 7, No. 3, pp. 355-369, 2006.
G. L. Semenza, "Targeting HIF-1 for cancer therapy", Nature Review-Cancer, vol. 3, pp. 721-732, 2003.
L. Li, X. Lin, A. R. Shoemaker, D. H. Albert, S. W. Fesik and Y. Shen, Clin, "Hypoxia-Inducible Factor-1 Inhibition in Combination with Temozolomide Treatment Exhibits Robust Antitumor Ef ficacy in vivo", Clin Cancer Res, vol. 12, No. 5, pp. 4747-4754, 2006.
B. J. Moeller, M. R. Dreher, Z. N. Rabbani, T. Schroeder, Y. Cao, C. Y. Li and M. W. Dewhirst, "Pleiotropic effects of HIF-1 blockade on tumor radiosensitivity", Cancer Cell, vol. 8, pp. 99-110, 2005.
U.S. National Institutes of Health database, ClinicalTrials.gov https://www.clinicaltrials.gov/, (accessed Aug. 20, 2015).
X. Huang, S. Gao, L. Fan, S. Yu and X. Liang, "Cytotoxic Alkaloids from the Roots of Tylophora atrofolliculata", Planta Med, vol. 70, pp. 441-445, 2004.

F. Abe, M. Hirokawa, T. Yamauchi, K. Honda, N. Hayashi, M. Ishii, S. Imagawa and M. Iwahana, "Further Investigation of Phenanthroindolizidine Alkalodis from Tylophora tanakae", Chem Pharm Bull, Vo. 46, No. 5, pp. 767-769, 1998.
F. Abe, Y. Iwase, T. Yamauchi, K. Honda and N. Hayashi, "Phenanthroindolizidine alkaloids from Tylophora tanakae", Phytochemistry, vol. 39, No. 3, pp. 695-699, 1995.
M. Ali, S. H. Ansari and J. S. Qadry, "Rare Phenanthroindolizidine Alkaloids and a Substituted Phenanthrene, Tyloindane, From Tylophira Indica", Journal of Natural Products, vol. 54, No. 5, pp. 1271-1278, 1991.
M. Ali and K. K. Bhutani, "Minor alkaloids of Tylophora hirsute", Phytochemistry, vol. 26, No. 7, pp. 2089-2092, 1987.
M. Ali and K. K. Bhutani, "Alkaloids from Tylophora indica", Phytochemistry, vol. 28, No. 12, pp. 3513-3517, 1989.
K. K. Bhutani, M. Ali and C. K. Atal, "13a hydroxytylophorine from tylophora hirsute", Phytochemistry, vol. 24, No. 11, pp. 2778-2780, 1985.
M. Dhiman, A. Khanna and S. Manju, "A new phenanthroindolizidine alkaloid from Tylophora indica", Chemical Papers, vol. 67, No. 2, pp. 245-248, 2013.
C. Gopalakrishnan, D. Shankaranarayanan, S. K. Nazimudeen and L. Kameswaran, "Effect of tylophorine, a major alkaloid of Tylophora indica, on immunopathological and inflammatory reactions", Indian J Med Res, vol. 71, pp. 940-948, 1980.
H. Y. Min, S. H. Song, B. Lee, S. Kim and S. K. Lee, "Inhibition of Lipopolysaccharide-Induced Nitric Oxide Production by Antofine and its Analogues in RAW 264.7 Macrophage Cells", Chemistry & Biodiversity, vol. 7, pp. 409-414, 2010.
M. Dhiman, R. R. Parab, S. L. Manju, D. C. Desai and G. B. Mahajan, "Antifungal activity of hydrochloride salts of tylophorinidine and tylophorinine", Nat Prod Commun., vol. 7, No. 9, pp. 1171-1172, 2012.
K. N. Rao and S. R. Venkatachalam, "Inhibition of Dihydrofolate Reductase and Cell Growth Activity by the Phenanthroindolizidine Alkaloids Pergularinine and Tylophorinidine: the In Vitro Cytotoxicity of These Plant Alkaloids and their Potential as Antimicrobial and Anticancer Agents", Toxicology in Vitro, vol. 14, pp. 53-59, 2000.
Y. Z. Lee, C. W. Huang, C. W. Yang, H. Y. Hsu, I. J. Kang, Y. S. Chao, I. S. Chen, H. Y. Chang and S. J. Lee, "Isolation and Biological Activities of Phenanthroindolizidine and Septicine Alkaloids from the Formosan Tylophora ovata", Planta Med, vol. 77, pp. 1932-1938, 2011.

(Continued)

*Primary Examiner* — Pancham Bakshi
(74) *Attorney, Agent, or Firm* — Renner Kenner Greive Bobak Taylor & Weber

(57) ABSTRACT

A method of isolating at least one phenanthroindolizidine alkaloid, in particular with HIF-1 inhibitory activity, from *Tylophora atrofolliculata* is used to isolate and obtain for example about 22 phenanthroindolizidine alkaloids, including at least 11 new phenanthroindolizidine alkaloids which have not been previously isolated. Experimental tests confirmed an exceptional HIF-1 inhibitory activity of the phenanthroindolizidine alkaloids isolated. A pharmaceutical composition includes at least one phenanthroindolizidine alkaloid and at least one pharmaceutical tolerable excipient. A method of treating a subject suffering from cancer includes administering at least one phenanthroindolizidine alkaloid isolated from *Tylophora atrofolliculata*. A method of treating a subject suffering from cancer includes administering at least one phenanthroindolizidine alkaloid to the subject.

3 Claims, 3 Drawing Sheets

(56) References Cited

OTHER PUBLICATIONS

Z. Wang, A. Feng, M. Cui, Y. Liu, L. Wang and Q. Wang, "First Discovery and Stucture Activity Relationship Study of Phenanthroquinolizidines as Novel Antiviral Agents against Tobacco Mosaic Virus (TMV)", PLOS One, vol. 7, No. 12, e52933, pp. 1-10, 2012.

M. Wu, G. Han, Z. Wang, Y. Liu and Q. Wang, "Synthesis and Antiviral Activities of Antofine Analogues with Different C-6 Substituent Groups", Journal of Agricultural and Food Chemistry, vol. 61, pp. 1030-1035, 2013.

X. F. Cai, X. Jin, D. Lee, Y. T. Yang, K. Lee, Y. S. Hong, J. H. Lee and J. J. Lee, "Phenanthroquinolizidine Alkaloids from the Roots of Boehmeria pannosa Potently Inhibit Hypoxia-Inducible Factor-1 in AGS Human Gastric Cancer Cells", J. Nat. Prod., vol. 69, pp. 1095-1097, 2006.

A. G. Damu, P. C. Kuo, L. S. Shi, C. Y. Li, C. R. Su and T. S. Wu, "Cytotoxic Phenanthroindolizidine Alkaloids from the Roots of Ficus septica", Planta Med., vol. 75, pp. 1152-1156, 2009.

A. G. Damu, P. C. Kuo, L. S. Shi, C. Y. Li, C. S. Kuoh, P. L. Wu and T. S. Wu, "Phenanthroindolizidine Alkaloids from the Stems of Ficus septica", J. Nat. Prod., vol. 68, pp. 1071-1075, 2005.

D. Stark, A. K. Lykkeberg, J. Christensen, B. A. Budnik, F. Abe and J. W. Jaroszewski, "In Vitro Cytotoxic Activity of Phenanthroindolizidine Alkaloids from Cynanchum vincetoxicum and Tylophora tanakae against Drug-Sensitive and Multidrug-Resistant Cancer Cells", J. Nat. Prod., vol. 65, pp. 1299-1302, 2002.

Jiangsu New Medical College, Dictionary of Chinese Traditional Medicine, Shanghai Scence and Technology Publishing House, Shanghai, vol. 80, No. 3, pp. 1747, 1977.

H. Lv, J. Ren, S. Ma, S. Xu, J. Qu, Z. Liu, Q. Zhou, X. Chen and S. Yu, "Synthesis Biological Evaluation and Mechanism Studies of Deoxytylophorinine and Its Derivatives as Potential Anticancer Agents", PLOS One, vol. 7, No. 1, e30342, pp. 1-16, 2012.

Y. Zhen, X. Huang, D. Yu and S. Yu, "Antitumor alkaloids isolated from Tylophora ovate", Acta Botanica Sinica, vol. 44, No. 3, pp. 349-353, 2002.

H. Komatsu, M. Watanabe, M. Ohyama, T. Enya, K. Koyama, T. Kanazawa, N. Kawahara, T. Sugimura and K. Wakabayashi, "Phenanthroindolizidine Alkaloids as Cytotoxic Substances in a Danaid Butterfly, Ideopsis similis, against Human Cancer Cells", J. Med. Chem., vol. 44, pp. 1833-1836, 2001.

D. Stærk, J. Christensen, E. Lemmich, J. Ø. Duus, C. E. Olsen and J. W. Jaroszewski,"Cytotoxic Activity of Some Phenanthroindolizidine N-Oxide Alkaloids from Cynanchum vincetoxicum", J. Nat. Prod., vol. 63, pp. 1584-1586, 2000.

J. F. Mi, S. D. Fang, Y. Chen, Y. M. Xu and R. Zhang, "The Application of Circular Dichroism on the Structure Analysis of Natural Products-Diterpenoid Dilactones and Tylophorines", Acta Pharmaceutica Sinica, vol. 27, No. 3, pp. 197-203, 1992.

Z. Wang and Q. Wang, "Highly efficient synthesis of phenanthroquinolizidine alkaloids via Parham type cycliacylation", Tetrahedron Letters, vol. 51, pp. 1377-1379, 2010.

H. Labaziewicz, F. G. Riddell and B. G. Sayer, "1, 2-Oxazine Chemistry, Part 6.+ Conformational Analysis of Cyclohexene and a Heterocyclic Analogue by (_13)C Nuclear Magnetic Resonance Spectroscopy", J. Chem. Soc., pp. 619-622, 1977.

T. F. Buckley and R. Henry, "α-Amino Acids as Chiral Eeducts for Asymmetric Products. Chirally Specific Syntheses of Tylophorine and Cryptopleurine", J. Org. Chem., vol. 48, No. 23, pp. 4222-4232, 1983.

M. Lavault, P. Richomme and J. Bruneton, "New phenatroindolizidine N-oxides alkaloids isolated from Vincetoxicum hirudinaria medic", Pharmaceutica Acta Helvetiae, vol. 68, pp. 225-227, 1994.

D. Nakano, K. Ishitsuka, M. Ikeda, R. Tsuchihashi, M. Okawa, H. Okabe, K. Tamura and J. Kinjo, "Screening of promising chemotherapeutic candidates from plants against human adult T-cell leukemia/lymphoma (IV): phenanthroindolizidine alkaloids from Tylophora tanakase leaves", J Nat Med, vol. 69, pp. 397-401, 2015.

H. Zhang, D. Z. Qian, Y. S. Tan, K. Lee, P. Gao, Y. R. Ren, S. Rey, H. Hammers, D. Chang, R. Pili, C. V. Dang, J. O. Liu and G. L. Semenza, "Digoxin and other cardiac glycosides inhibit HIF synthesis and block tumor growth", PNAS, vol. 105, No. 50, pp. 19579-19586, 2008.

G. Melillo, "Inhibiting Hypoxia-Inducible Factor 1 for Cancer Therapy", Mol Cancer Res, vol. 4, No. 9, pp. 601-605, 2006.

T. W. Hodges, C. F. Hossain, Y.-P. Kim, Y.-D. Zhou and D. G. Nagle, "Molecular-Targeted Antitumor Agents: The Saururus cernuus Dineolignans Manassantin B and 4-O-Demethylmanassantin B Are Potent Inhibitors of Hypoxia-Activated HIF-1", J. Nat. Prod., vol. 67, No. 5, pp. 767-771, 2004.

S. Parhira, G.-Y. Zhu, R.-W. Jiang, L. Liu, L.-P. Bai and Z.-H. Jiang, "2'-Epi-uscharin from the Latex of Calotropis gigantea with HIF-1 Inhibitory Activity", Scientific Report, vol. 4, No. 4748, pp. 1-7, 2014.

* cited by examiner

METHOD OF ISOLATING PHENANTHROINDOLIZIDINE ALKALOIDS FROM *TYLOPHORA ATROFOLLICULATA* WITH HIF-1 INHIBITORY ACTIVITY, COMPOSITIONS COMPRISING THEM AND THEIR USE

The present invention provides a method of isolating at least one phenanthroindolizidine alkaloid in particular with HIF-1 inhibitory activity from *Tylophora atrofolliculata*. The present invention further refers to a composition, in particular a pharmaceutical composition, comprising the at least one phenanthroindolizidine alkaloid and at least one excipient. Still further, the present invention refers to a method of treating a subject suffering from cancer by administering at least one phenanthroindolizidine alkaloid isolated from *Tylophora atrofolliculata*. In accordance with the invention is also a method of treating a subject suffering from cancer by administering at least one phenanthroindolizidine alkaloid of certain chemical formula to the subject.

BACKGROUND OF THE INVENTION

Rapid tumor growth is accompanied by an unbalance between oxygen supply and consumption resulting in low oxygen levels and thus the existence of hypoxic regions. Tumor hypoxia is not only the major problem for radiotherapy treatment failure and anticancer drug resistance, but also an indicator for advanced disease stages, disease relapse and poor prognosis (J. M. Brown, Cancer Res., 1999, 59, 5863-5870). The transcription factor HIF-1 (Hypoxia-inducible factor-1) plays a significant role in cellular adaption and survival under hypoxic condition (D. G. Nagle and Y. D. Zhou, Curr. drug targets, 2006, 7, 355-369). Preclinical studies indicate that the inhibition of HIF-1 activity has a remarkable impact on tumor growth (G. L. Semenza, Nat. Rev. Cancer, 2003, 3, 721-732). Besides, combination of HIF-1 inhibition with chemotherapeutic agents/radiation gives rise to improved treatment outcomes (Li, L. et al., Clin. Cancer Res., 2006, 12, 4747-4754, Moeller, B. J. et al., Cancer Cell, 2005, 8, 99-110). Consequently, HIF-1 represents a promising target for cancer therapy. Presently, early phase clinical trials with topotecan, a natural product-derived topoisomerase-1/HIF-1 inhibitor, have been completed. Moreover, digoxin has entered phase two clinical trial as novel HIF-1 inhibitor, which exhibits the prospect of developing HIF-1 targeted anticancer drugs.

There remains a strong need for therapeutically effective compounds and improved ways for successfully treating cancer, wherein inhibiting HIF-1 represents a highly promising approach as explained above. As usual, it would generally be desirable to have compounds with reduced risk for side effects, which can be prepared in a cost-effective way and are directed only at tumor cells.

Recently, Traditional Chinese medicine as well as complementary and alternative medicine has getting popular providing a lot of treatment options. Traditional Chinese medicines based on plant materials as well as plants or respective components gained from plants usually allow for treatment of various diseases and conditions while bearing a reduced risk for side effects. In view of the rich medicinal plant resources, available respective medicines can usually be produced in a cost-effective way. Accordingly, there has been a lot of research with regard to plants and respective ingredients for treatment of several diseases and conditions.

For example, *Tylophora atrofolliculata* (Asclepiadaceae) is already used as a traditional medicine. The roots of *Tylophora atrofolliculata* which are mainly distributed in the Guangxi Province in the Southwest of China have been used such as for the treatment of rheumatism. Components isolated from said plant include phenanthroindolizidine alkaloids (Huang, X. et al., Planta Med., 2004, 70, 441-445, Abe, F. et al., Chem. Pharm. Bull, 1998, 46, 767-769, Abe, F. et al., Phytochemistry, 1995, 39, 695-699, Ali, M. et al., J. Nat. Prod., 1991, 54, 1271-1278, M. Ali and K. K. Bhutani, Phytochemistry, 1987, 26, 2089-2092, Ali, M. and Bhutani, K. K., Phytochemistry, 1989, 28, 3513-3517, Bhutani, K. K. et al., Phytochemistry, 1985, 24, 2778-2780, Dhiman, M. et al., Chem. Pap.-Chem. Zvesti, 2013, 67, 245-248), however, only alkaloids such as tylophoridicine C-F, tylophorinine, tylophorinidine have been isolated from this plant so far. Members of the phenanthroindolizidine alkaloid class are generally well known to possess multiple pharmacological effects, such as anti-inflammatory, antifungal, antibacterial, and antiviral activities. Besides, pronounced cytotoxicity of some phenanthroindolizidine alkaloids against various cancer cell lines attracted much attention in the discovery of anticancer drugs (Lee, Y. Z. et al., Planta Med., 2011, 77, 1932-1938, Cai, X. F. et al., J. Nat. Prod., 2006, 69, 1095-1097, Damu, A. G. et al., Planta Med., 2009, 75, 1152-1156, Damu, A. G. et al., J. Nat. Prod., 2005, 68, 1071-1075, Lykkeberg, A. K. et al., J. Nat. Prod., 2002, 65, 1299-1302).

In view of the presence of various different compounds in plants usually with completely different mode of action and therapeutic efficiency, there is a strong need for identifying and providing components in isolated form with suitable therapeutic efficiency such as with sufficient HIF-1 inhibitory activity for treatment of cancer. Having those active ingredients in isolated form could further reduce the risk of side effects or interactions resulting from the presence of further compounds limiting the therapeutic use.

SUMMARY OF THE INVENTION

The invention provides in a first aspect a method of isolating at least one phenanthroindolizidine alkaloid in particular with HIF-1 inhibitory activity from *Tylophora atrofolliculata* which method comprises steps of:

(i) subjecting *Tylophora atrofolliculata* plant material to a solvent extraction with an extraction solvent for obtaining a crude extract, wherein the extraction solvent comprises an aliphatic alcohol;

(ii) contacting the crude extract with a first and a second separation solvent for obtaining a first and second layer, wherein the first separation solvent comprises water and the second separation solvent comprises an ester;

(iii) contacting the first layer with a third separation solvent comprising a halogenated hydrocarbon for forming a third layer;

(iv) subjecting the third layer to at least a first chromatographic separation step, in particular carried out with liquid column chromatography including separating by means of fragmentation.

Preferably, the at least one phenanthroindolizidine alkaloid is selected from a compound:

having Formula (I):

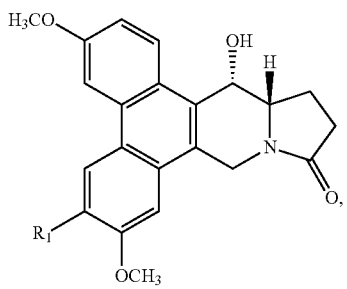

Formula (I)

wherein $R_1$ is OH (also referenced as compound (1));

having Formula (I) above, wherein $R_1$ is $OCH_3$ (also referenced as compound (2));

having Formula (II):

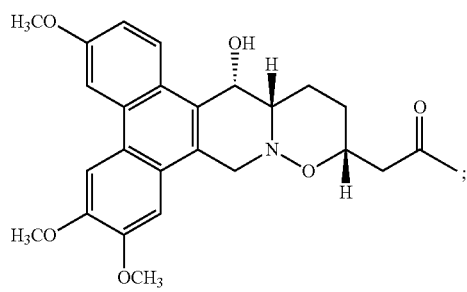

Formula (II)

(also referenced as compound (3))

having Formula (III):

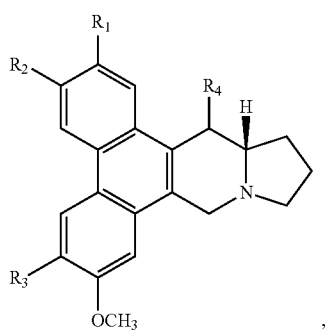

Formula (III)

wherein $R_1$ is OH, $R_2$ is $OCH_3$, $R_3$ is OH and $R_4$ is H (also referenced as compound (4));

having Formula (III) above, wherein $R_1$ is OH, $R_2$ is $OCH_3$, $R_3$ is OH and $R_4$ is α-OH (also referenced as compound (5));

having Formula (III) above, wherein $R_1$ is H, $R_2$ is OH, $R_3$ is OH and $R_4$ is α-OH (also referenced as compound (13));

having Formula (III) above, wherein $R_1$ is H, $R_2$ is $OCH_3$, $R_3$ is OH and $R_4$ is α-OH (also referenced as compound (14));

having Formula (III) above, wherein $R_1$ is H, $R_2$ is OH, $R_3$ is $OCH_3$ and $R_4$ is α-OH (also referenced as compound (15));

having Formula (III) above, wherein $R_1$ is H, $R_2$ is $OCH_3$, $R_3$ is $OCH_3$ and $R_4$ is β-OH (also referenced as compound (18));

having Formula (III) above, wherein $R_1$ is $OCH_3$, $R_2$ is $OCH_3$, $R_3$ is $OCH_3$ and $R_4$ is H (also referenced as compound (19));

having Formula (III) above, wherein $R_1$ is H, $R_2$ is $OCH_3$, $R_3$ is $OCH_3$ and $R_4$ is H (also referenced as compound (20));

having Formula (III) above, wherein $R_1$ is H, $R_2$ is $OCH_3$, $R_3$ is $OCH_3$ and $R_4$ is α-OH (also referenced as compound (21));

having Formula (IV):

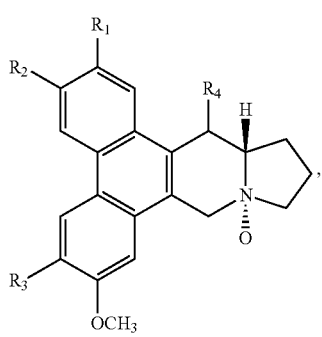

Formula (IV)

wherein $R_1$ is H, $R_2$ is OH, $R_3$ is OH and $R_4$ is β-OH (also referenced as compound (6));

having Formula (IV) above, wherein $R_1$ is OH, $R_2$ is $OCH_3$, $R_3$ is $OCH_3$ and $R_4$ is β-OH (also referenced as compound (8));

having Formula (IV) above, wherein $R_1$ is $OCH_3$, $R_2$ is $OCH_3$, $R_3$ is $OCH_3$ and $R_4$ is α-OH (also referenced as compound (10));

having Formula (IV) above, wherein $R_1$ is $OCH_3$, $R_2$ is $OCH_3$, $R_3$ is $OCH_3$ and $R_4$ is H (also referenced as compound (11));

having Formula (IV) above, wherein $R_1$ is H, $R_2$ is $OCH_3$, $R_3$ is $OCH_3$ and $R_4$ is H (also referenced as compound (12));

having Formula (V):

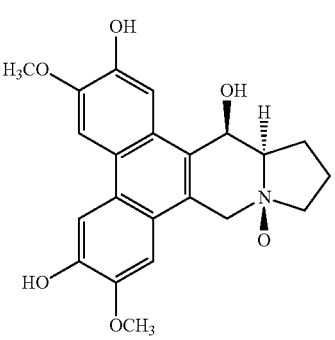

Formula (V)

(also referenced as compound (7))

having Formula (VI):

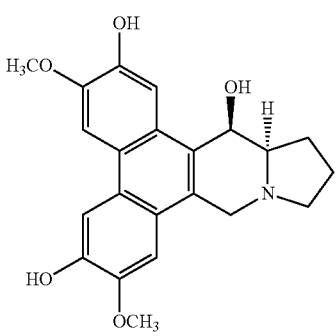

Formula (VI)

(also referenced as compound (9))

having Formula (VII):

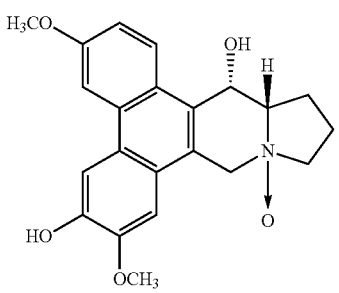

Formula (VII)

(also referenced as compound (16))

having Formula (VIII):

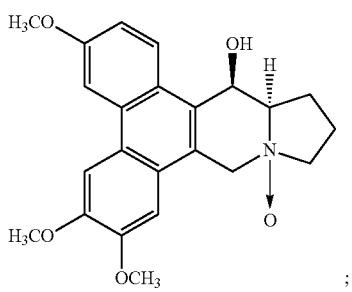

Formula (VIII)

(also referenced as compound (17))

or a compound having Formula (IX):

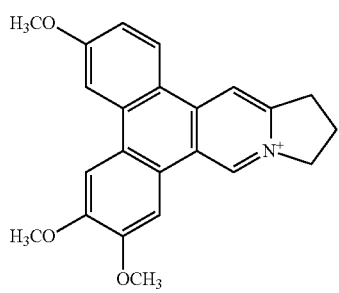

Formula (IX)

(also referenced as compound (22)).

The present invention further refers to a method of treating a subject suffering from cancer, in particular breast cancer, comprising administering an effective amount of at least one phenanthroindolizidine alkaloid isolated from *Tylophora atrofolliculata* according to the method described before to the subject. The phenanthroindolizidine alkaloid can be selected from the group consisting of a phenanthroindolizidine alkaloid:
  having Formula (III) given above, wherein $R_1$ is OH, $R_2$ is $OCH_3$, $R_3$ is OH and $R_4$ is H;
  having Formula (III), wherein $R_1$ is OH, $R_2$ is $OCH_3$, $R_3$ is OH and $R_4$ is α-OH;
  having Formula (III), wherein $R_1$ is H, $R_2$ is OH, $R_3$ is OH and $R_4$ is α-OH;
  having Formula (III), wherein $R_1$ is H, $R_2$ is $OCH_3$, $R_3$ is OH and $R_4$ is α-OH;
  having Formula (III), wherein $R_1$ is H, $R_2$ is OH, $R_3$ is $OCH_3$ and $R_4$ is α-OH;
  having Formula (III), wherein $R_1$ is H, $R_2$ is $OCH_3$, $R_3$ is $OCH_3$ and $R_4$ is β-OH;
  having Formula (III), wherein $R_1$ is H, $R_2$ is $OCH_3$, $R_3$ is $OCH_3$ and $R_4$ is H;
  having Formula (III), wherein $R_1$ is H, $R_2$ is $OCH_3$, $R_3$ is $OCH_3$ and $R_4$ is α-OH;
  having Formula (IV) given above, wherein $R_1$ is H, $R_2$ is OH, $R_3$ is OH and $R_4$ is β-OH;
  having Formula (IV), wherein $R_1$ is OH, $R_2$ is $OCH_3$, $R_3$ is $OCH_3$ and $R_4$ is β-OH;
  having Formula (IV), wherein $R_1$ is H, $R_2$ is $OCH_3$, $R_3$ is $OCH_3$ and $R_4$ is H;
  having Formula (V) given above;
  having Formula (VII) given above;
  or having Formula (VIII) given above.

The phenanthroindolizidine alkaloid administered in particular has one of the following Formulas:
  Formula (III) given above, wherein $R_1$ is OH, $R_2$ is $OCH_3$, $R_3$ is OH and $R_4$ is H;
  Formula (III), wherein $R_1$ is OH, $R_2$ is $OCH_3$, $R_3$ is OH and $R_4$ is α-OH;
  Formula (IV) given above, wherein $R_1$ is H, $R_2$ is OH, $R_3$ is OH and $R_4$ is β-OH;
  Formula (IV), wherein $R_1$ is OH, $R_2$ is $OCH_3$, $R_3$ is $OCH_3$ and $R_4$ is β-OH;
  Formula (IV), wherein $R_1$ is H, $R_2$ is $OCH_3$, $R_3$ is $OCH_3$ and $R_4$ is H;
  Formula (V) given above.

Still further, the present invention refers to a composition, preferably a pharmaceutical composition, comprising and in particular essentially consisting of:
  at least one, in particular one phenanthroindolizidine alkaloid, in particular as pharmaceutically effective ingredient, isolated from *Tylophora atrofolliculata* according to the method described above, and
  at least one pharmaceutically tolerable excipient such as one or more of a diluent, a filler, a binder, a disintegrant, a lubricant, a coloring agent, a surfactant and a preservative.

Another aspect of the present invention relates to a method of treating a subject suffering from cancer comprising:
  isolating a phenanthroindolizidine alkaloid from *Tylophora atrofolliculata* by the method described above, in particular a phenanthroindolizidine alkaloid:
    having Formula (III) given above, wherein $R_1$ is OH, $R_2$ is $OCH_3$, $R_3$ is OH and $R_4$ is H;
    having Formula (III), wherein $R_1$ is OH, $R_2$ is $OCH_3$, $R_3$ is OH and $R_4$ is α-OH;

having Formula (IV) given above, wherein $R_1$ is H, $R_2$ is OH, $R_3$ is OH and $R_4$ is β-OH;

having Formula (IV), wherein $R_1$ is OH, $R_2$ is $OCH_3$, $R_3$ is $OCH_3$ and $R_4$ is β-OH;

having Formula (IV), wherein $R_1$ is H, $R_2$ is $OCH_3$, $R_3$ is $OCH_3$ and $R_4$ is H;

or having Formula (V) given above;

formulating the phenanthroindolizidine alkaloid into a pharmaceutically composition; and administering said pharmaceutical composition to a subject suffering from cancer.

The subject is preferably a human. The cancer is preferably breast cancer. Further in accordance with the present invention is the at least one phenanthroindolizidine alkaloid isolated from *Tylophora atrofolliculata* for use in the treatment of cancer like breast cancer and the use of the at least one phenanthroindolizidine alkaloid isolated from *Tylophora atrofolliculata* for preparing a medicament for the treatment of cancer like breast cancer.

Another aspect concerns a method of treating a subject suffering from cancer comprising administering at least one phenanthroindolizidine alkaloid isolated from *Tylophora atrofolliculata* with the method described above in combination with radiotherapy in particular with X-rays or chemotherapy, i.e. with further active ingredients for treating cancer.

Still further, the present invention relates to a compound selected from the group consisting of:
a compound having Formula (I) given above, wherein $R_1$ is OH;
a compound having Formula (II) given above;
a compound having Formula (III) given above, wherein $R_1$ is OH, $R_2$ is $OCH_3$, $R_3$ is OH and $R_4$ is H;
a compound having Formula (III), wherein $R_1$ is OH, $R_2$ is $OCH_3$, $R_3$ is OH and $R_4$ is α-OH;
a compound having Formula (IV) given above, wherein $R_1$ is H, $R_2$ is OH, $R_3$ is OH and $R_4$ is β-OH;
a compound having Formula (IV), wherein $R_1$ is OH, $R_2$ is $OCH_3$, $R_3$ is $OCH_3$ and $R_4$ is β-OH;
a compound having Formula (IV), wherein $R_1$ is $OCH_3$, $R_2$ is $OCH_3$, $R_3$ is $OCH_3$ and $R_4$ is α-OH;
a compound having Formula (IV), wherein $R_1$ is $OCH_3$, $R_2$ is $OCH_3$, $R_3$ is $OCH_3$ and $R_4$ is H;
a compound having Formula (IV), wherein $R_1$ is H, $R_2$ is $OCH_3$, $R_3$ is $OCH_3$ and $R_4$ is H;
a compound having Formula (V) given above;
and a compound having Formula (VI).

In still another aspect, the present invention refers to a method for targeting cancer cells in particular breast cancer cells. Said method comprises the step of contacting a population of cancer cells with at least one and preferably one phenanthroindolizidine alkaloid isolated from *Tylophora atrofolliculata* as described above.

The method of the present invention of isolating at least one phenanthroindolizidine alkaloid from *Tylophora atrofolliculata* can be used to isolate and obtain for example about 22 phenanthroindolizidine alkaloids. Among them are 11 new phenanthroindolizidine alkaloids, namely compounds (1) and (3) to (12), which have not been previously isolated and which include phenanthroindolizidine alkaloids firstly identified in *Tylophora* genus like compounds (4), (5), (7) to (9).

Most phenanthroindolizidine alkaloids isolated with the method of the present invention exhibited extremely potent inhibitory effects on HIF-1 with $IC_{50}$ values in the low nanomolar range without significant cytotoxicity. The potency of several phenanthroindolizidine alkaloids isolated was even comparable to Manassantin B ($IC_{50}$ 3 nM), the most potent natural HIF-1 inhibitor identified so far. Finally, the HIF-1 inhibitory effects measured revealed the prerequisites for high active alkaloids, including non-planarity at indolizidine moiety, substitution types and patterns on the phenanthrene and indolizidine moieties. Summing up, the present invention provides plant-derived phenanthroindolizidine alkaloids with exceptional HIF-1 inhibitory activity suitable to represent lead compounds for the discovery of further HIF-1 inhibitors.

Other features and aspects of the invention will become apparent by consideration of the following detailed description and accompanying drawings.

DESCRIPTION OF THE EMBODIMENTS

Figure 1A:
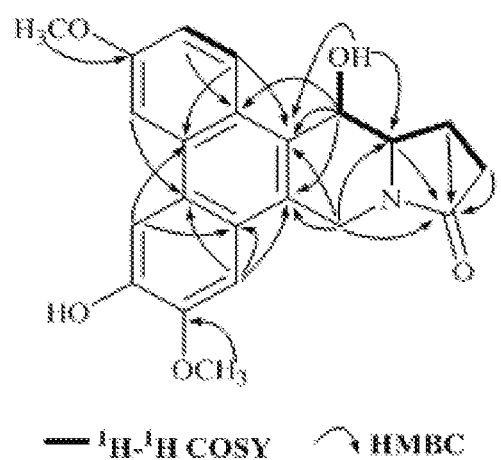
FIG. 1A and FIG. 1B show the key correlations observed in $^1$H-$^1$H COSY, HMBC, and NOESY spectra of compound (1), respectively.

The following preparations and examples are given to enable those skilled in the art to more clearly understand and to practice the present invention. They should not be considered as limiting the scope of the invention, but merely as being illustrative and for representing preferred embodiments thereof. The technical terms used in the present patent application have the meaning as commonly understood by a respective skilled person unless specifically defined otherwise.

As used herein and in the claims, "comprising" means including the following elements but not excluding others. "Essentially consisting of" means that the material consists of the respective element along with usually and unavoidable impurities such as side products and components usually resulting from the respective preparation or method for obtaining the material such as traces of further components or solvents. "Consisting of" means that the material solely consists of, i.e. is formed by the respective element.

In a first aspect, the invention provides a method of isolating at least one phenanthroindolizidine alkaloid in particular with HIF-1 inhibitory activity from *Tylophora atrofolliculata*. The method of the present invention comprises steps of:

(i) subjecting *Tylophora atrofolliculata* plant material to a solvent extraction with an extraction solvent for obtaining a crude extract, wherein the extraction solvent comprises an aliphatic alcohol;

(ii) contacting the crude extract with a first and a second separation solvent for obtaining a first and second layer, wherein the first separation solvent comprises water and the second separation solvent comprises an ester;

(iii) contacting the first layer with a third separation solvent comprising a halogenated hydrocarbon for forming a third layer;

(iv) subjecting the third layer to at least a first chromatographic separation step.

Optionally, the method includes further steps after step (iv) of purifying the at least one phenanthroindolizidine alkaloid.

The term "isolating" or "isolation" used herein means separating a combination of two or more or one single phenanthroindolizidine alkaloid from components present in the *Tylophora atrofolliculata* plant material. In particular, the method is for isolating a combination of at most 10, further preferred at most 5, still further preferred at most two and in particular one single phenanthroindolizidine alkaloid, in particular an phenanthroindolizidine alkaloid with HIF-1 inhibitory activity, from *Tylophora atrofolliculata* plant material.

The term "purifying" as used herein refers to methods generally known to the skilled person for purifying compounds like evaporation, lyophilization or (re-)crystallization for obtaining a desired degree of purity, i.e. a desired degree of absence of impurities.

The at least one ingredient isolated from *Tylophora atrofolliculata* plant material is a phenanthroindolizidine alkaloid. "Alkaloids" are known to the skilled person as a class of components present in various plants characterized by a chemical structure with at least one nitrogen atom, usually at least one heterocyclic nitrogen atom. Alkaloids can be divided into several subgroups depending on the specific nitrogen containing heterocyclic ring system. Phenanthroindolizidine alkaloids represent a small subgroup of alkaloids and the term generally refers to compounds having a phenanthrene ring system fused with that of an indolizidine.

Preferably, the at least one phenanthroindolizidine alkaloid is selected from a compound:

having Formula (I):

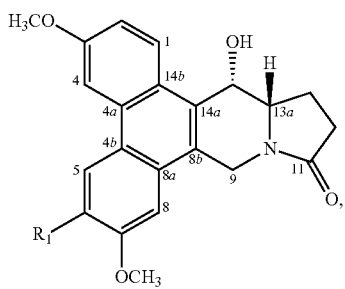

Formula (I)

wherein $R_1$ is selected from OH or $OCH_3$;

having Formula (II):

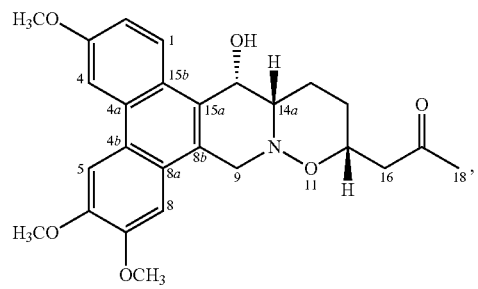

Formula (II)

having Formula (III):

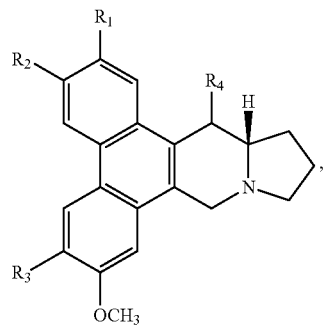

Formula (III)

wherein $R_1$ is selected from OH, H or $OCH_3$, $R_2$ is selected from $OCH_3$ or OH. $R_3$ is selected from $OCH_3$ or OH and $R_4$ is selected from α-OH, β-OH or H;

having Formula (IV):

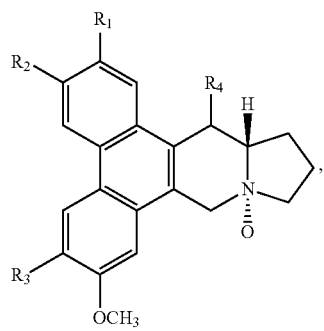

Formula (IV)

wherein $R_1$ is selected from OH, H or $OCH_3$, $R_2$ is selected from $OCH_3$ or OH, $R_3$ is selected from $OCH_3$ or OH and $R_4$ is selected from α-OH, β-OH or H;

having Formula (V):

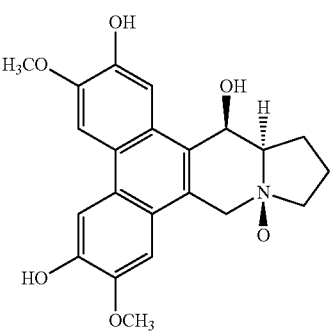

Formula (V)

having Formula (VI):

Formula (VI)

having Formula (VII):

Formula (VII)

having Formula (VIII):

Formula (VIII)

or a compound having Formula (IX):

Formula (IX)

More preferably, the at least one phenanthroindolizidine alkaloid is selected from a compound:
having Formula (I) given above, wherein $R_1$ is OH (also referenced as compound (1));

having Formula (I), wherein $R_1$ is $OCH_3$ (also referenced as compound (2));

having Formula (II) given above (also referenced as compound (3));

having Formula (III) given above, wherein $R_1$ is OH, $R_2$ is $OCH_3$, $R_3$ is OH and $R_4$ is H (also referenced as compound (4));

having Formula (III), wherein $R_1$ is OH, $R_2$ is $OCH_3$, $R_3$ is OH and $R_4$ is α-OH (also referenced as compound (5));

having Formula (III), wherein $R_1$ is H, $R_2$ is OH, $R_3$ is OH and $R_4$ is α-OH (also referenced as compound (13));

having Formula (III), wherein $R_1$ is H, $R_2$ is $OCH_3$, $R_3$ is OH and $R_4$ is α-OH (also referenced as compound (14));

having Formula (III), wherein $R_1$ is H, $R_2$ is OH, $R_3$ is $OCH_3$ and $R_4$ is α-OH (also referenced as compound (15));

having Formula (III), wherein $R_1$ is H, $R_2$ is $OCH_3$, $R_3$ is $OCH_3$ and $R_4$ is β-OH (also referenced as compound (18));

having Formula (III), wherein $R_1$ is $OCH_3$, $R_2$ is $OCH_3$, $R_3$ is $OCH_3$ and $R_4$ is H (also referenced as compound (19));

having Formula (III), wherein $R_1$ is H, $R_2$ is $OCH_3$, $R_3$ is $OCH_3$ and $R_4$ is H (also referenced as compound (20));

having Formula (III), wherein $R_1$ is H, $R_2$ is $OCH_3$, $R_3$ is $OCH_3$ and $R_4$ is α-OH (also referenced as compound (21));

having Formula (IV) given above, wherein $R_1$ is H, $R_2$ is OH, $R_3$ is OH and $R_4$ is β-OH (also referenced as compound (6));

having Formula (IV), wherein $R_1$ is OH, $R_2$ is $OCH_3$, $R_3$ is $OCH_3$ and $R_4$ is β-OH (also referenced as compound (8));

having Formula (IV), wherein $R_1$ is $OCH_3$, $R_2$ is $OCH_3$, $R_3$ is $OCH_3$ and $R_4$ is α-OH (also referenced as compound (10));

having Formula (IV), wherein $R_1$ is $OCH_3$, $R_2$ is $OCH_3$, $R_3$ is $OCH_3$ and $R_4$ is H (also referenced as compound (11));

having Formula (IV), wherein $R_1$ is H, $R_2$ is $OCH_3$, $R_3$ is $OCH_3$ and $R_4$ is H (also referenced as compound (12));

having Formula (V) given above (also referenced as compound (7));

having Formula (VI) given above (also referenced as compound (9));

having Formula (VII) given above (also referenced as compound (16));

having Formula (VIII) given above (also referenced as compound (17));

or a compound having Formula (IX) given above (also referenced as compound (22)).

In particular, the method of the present invention allows for the isolation of at least one of the following phenanthroindolizidine alkaloids, i.e. at least one of the following phenanthroindolizidine alkaloids is isolated from *Tylophora atrofolliculata* with the method of the present invention:

a phenanthroindolizidine alkaloid having Formula (I) given above, wherein $R_1$ is OH, a phenanthroindolizidine alkaloid having Formula (II) given above;

a phenanthroindolizidine alkaloid having Formula (III) given above, wherein $R_1$ is OH, $R_2$ is $OCH_3$, $R_3$ is OH and $R_4$ is H;

a phenanthroindolizidine alkaloid having Formula (III), wherein $R_1$ is OH, $R_2$ is $OCH_3$, $R_3$ is OH and $R_4$ is α-OH;

a phenanthroindolizidine alkaloid having Formula (IV) given above, wherein $R_1$ is H, $R_2$ is OH, $R_3$ is OH and $R_4$ is β-OH;

a phenanthroindolizidine alkaloid having Formula (IV), wherein $R_1$ is OH, $R_2$ is $OCH_3$, $R_3$ is $OCH_3$ and $R_4$ is β-OH;

a phenanthroindolizidine alkaloid having Formula (IV), wherein $R_1$ is $OCH_3$, $R_2$ is $OCH_3$, $R_3$ is $OCH_3$ and $R_4$ is α-OH;

a phenanthroindolizidine alkaloid having Formula (IV), wherein $R_1$ is $OCH_3$, $R_2$ is $OCH_3$, $R_3$ is $OCH_3$ and $R_4$ is H;

a phenanthroindolizidine alkaloid having Formula (IV), wherein $R_1$ is H, $R_2$ is $OCH_3$, $R_3$ is $OCH_3$ and $R_4$ is H;

a phenanthroindolizidine alkaloid having Formula (V) given above;

or a phenanthroindolizidine alkaloid having Formula (VI) given above.

In still more preferred embodiments of the present invention, the method of the present invention allows for the isolation of at least one of the following phenanthroindolizidine alkaloids, i.e. at least one of the following phenanthroindolizidine alkaloids is more preferably isolated, in particular one of the following phenanthroindolizidine alkaloids:

a phenanthroindolizidine alkaloid having Formula (III) given above, wherein $R_1$ is OH, $R_2$ is $OCH_3$, $R_3$ is OH and $R_4$ is H;

a phenanthroindolizidine alkaloid having Formula (III), wherein $R_1$ is OH, $R_2$ is $OCH_3$, $R_3$ is OH and $R_4$ is α-OH;

a phenanthroindolizidine alkaloid having Formula (IV) given above, wherein $R_1$ is H, $R_2$ is OH, $R_3$ is OH and $R_4$ is β-OH;

a phenanthroindolizidine alkaloid having Formula (IV), wherein $R_1$ is OH, $R_2$ is $OCH_3$, $R_3$ is $OCH_3$ and $R_4$ is β-OH;

a phenanthroindolizidine alkaloid having Formula (IV), wherein $R_1$ is H, $R_2$ is $OCH_3$, $R_3$ is $OCH_3$ and $R_4$ is H;

or a phenanthroindolizidine alkaloid having Formula (V) given above.

In most preferred embodiments of the present invention, the method of the present invention allows for the isolation of one of the following phenanthroindolizidine alkaloids, i.e. one of the following phenanthroindolizidine alkaloids is most preferably isolated with the method of the present invention:

a phenanthroindolizidine alkaloid having Formula (III) given above, wherein $R_1$ is OH, $R_2$ is $OCH_3$, $R_3$ is OH and $R_4$ is H;

a phenanthroindolizidine alkaloid having Formula (III), wherein $R_1$ is OH, $R_2$ is $OCH_3$, $R_3$ is OH and $R_4$ is α-OH;

a phenanthroindolizidine alkaloid having Formula (IV) given above, wherein $R_1$ is H, $R_2$ is OH, $R_3$ is OH and $R_4$ is β-OH;

or a phenanthroindolizidine alkaloid having Formula (V) given above.

In especially preferred embodiments of the present invention, one of the phenanthroindolizidine alkaloids of Formula (III) with $R_1$ being OH, $R_2$ being $OCH_3$, $R_3$ being OH and $R_4$ being H or of Formula (III) with $R_1$ being OH, $R_2$ being $OCH_3$, $R_3$ being OH and $R_4$ being α-OH is isolated with the method of the present invention.

The method of the present invention comprises a step (i) of subjecting *Tylophora atrofolliculata* plant material to a solvent extraction with an extraction solvent for obtaining a crude extract, wherein the extraction solvent comprises an aliphatic alcohol.

Preferably, the *Tylophora atrofolliculata* plant material comprises the whole plant, i.e. it comprises roots and aerial parts of *Tylophora atrofolliculata*. The method of the present invention may further comprise steps before carrying out step (i) of a) drying the *Tylophora atrofolliculata* plant material, and/or
b) cutting, shredding, milling and/or pulverizing the *Tylophora atrofolliculata* plant material.

For example, about 1 kg to 10 kg such as about 5.5 kg of the *Tylophora atrofolliculata* plant material can be used in the method of the present invention. The amount of *Tylophora atrofolliculata* plant material in relation to the total amount of the extraction solvent used in step (i) is preferably between 20 mg/ml and 60 mg/ml, further preferred about 42 mg/ml plant material relative to the total amount of extraction solvent used in step (i). In embodiments, in which the solvent extraction in step (i) is carried out three times, the amount of *Tylophora atrofolliculata* plant material in relation to the amount of extraction solvent in each of the three solvent extractions is preferably of from 80 to 180 mg/ml, more preferably in the first solvent extraction about 100 mg/ml, in the second solvent extraction about 125 mg/ml and in the third solvent extraction about 167 mg/ml, wherein the amount of extraction solvent in the second and third solvent extraction is calculated in relation to the starting weight of the *Tylophora atrofolliculata* plant material used in the first solvent extraction.

The extraction solvent comprises an aliphatic alcohol, which means herein an aliphatic hydrocarbon, preferably a branched or straight chain alkane, wherein at least one hydrogen atom of the aliphatic hydrocarbon is substituted with a hydroxyl group, preferably one hydrogen atom is substituted with a hydroxyl group referenced as monohydric aliphatic alcohol. More preferably, the aliphatic alcohol of the extracting solvent is a monohydric aliphatic alcohol, still more preferably a monohydric alcohol with 1 to 4 carbon atoms, further preferably with 1 to 2 carbon atoms. I.e. the aliphatic alcohol of the first extracting solvent is more preferably selected from methanol, ethanol, propanol, iso-propanol, n-butanol, isobutanol, sec-butyl alcohol, tert-butyl alcohol or mixtures thereof and further preferably from methanol, ethanol or mixtures thereof. More preferably, the aliphatic alcohol of the extraction solvent is methanol. The extraction solvent most preferably essentially consists of methanol.

The solvent extraction in step (i) is preferably carried out for 4 to 10 h in total. In embodiments, in which the solvent extraction in step (i) is carried out three times, each of the three solvent extractions is carried out for 2 to 4 h, more preferably the first solvent extraction is carried out for about 4 h, the second solvent extraction for about 2 h and the third solvent extraction for about 2 h.

The temperatures are preferably above 45° C., in particular at least 50° C., and most preferably the *Tylophora atrofolliculata* plant material is refluxed with the first extraction solvent.

The solvent extraction in step (i) is preferably carried out at least two, more preferably at least three times and in particular three times, wherein the extracts obtained in each step are combined for forming the crude extract. Thus, in especially preferred embodiments of the present invention, the *Tylophora atrofolliculata* plant material is refluxed with the extraction solvent, in particular methanol, at least two times, in particular three times. I.e. the solvent extraction is preferably carried out three times with the *Tylophora atrofolliculata* plant material.

Preferably, the extraction solvent is removed before step (ii) for forming the crude extract, i.e. step (i) preferably further comprises removing the extraction solvent after the solvent extraction and before step (ii). The extraction solvent is preferably removed by evaporation under reduced pressure.

The method of the present invention further comprises a step (ii) of contacting the crude extract obtained in step (i) with a first and a second separation solvent for obtaining a first and a second layer, wherein the first separation solvent comprises and preferably essentially consists of water and the second separation solvent comprises an ester. The ester is in particular a $C_1$-$C_6$ aliphatic alcohol ester of a $C_1$-$C_7$ alkyl carboxylic acid. Further preferably, the ester is a $C_3$-$C_7$ ester, in particular ethyl acetate or ethyl formate. In most preferred embodiments of the present invention, the second separation solvent comprises and preferably essentially consists of ethyl acetate. In particular, the first separation solvent is mainly comprised in the first layer and the second separation solvent is mainly comprised in the second layer obtained. More specifically, the first layer in particular comprises the at least one phenanthroindolizidine alkaloid and the main part of the first separation solvent. The second layer comprises the main part of the second separation solvent. "Main part" usually means more than 90% of the total amount of the separation solvent, preferably more than 95%. The term "layers" used herein and as generally understood by the skilled person means separated phases resulting from contacting at least two solvents which are substantially immiscible or immiscible with each other, in the present invention for example the first and the second separation solvent.

Preferably, contacting the crude extract with the first and the second separation solvent in step (ii) means sequentially adding the first and the second separation solvent to the crude extract. In preferred embodiments of the present invention, the crude extract is added, preferably suspended, in the first separation solvent. Preferably, the pH of the suspension is adjusted to less than 3, in particular to about 1 to 2 before adding the second separation solvent, preferably by adding an inorganic (mineral) acid, in particular by adding HCl. Then the second separation solvent is preferably added accompanied by shaking for forming the first and the second layer and the first layer is then separated. Such procedure is especially suitable for separating chlorophyll and neutral compounds from the phenanthroindolizidine alkaloids.

Preferably, the pH of the first layer is adjusted to at least pH 8 by adding a base before step (iii), in particular by adding an alkali hydroxide. I.e. the base is preferably an alkali hydroxide. Alkali hydroxides are a class of chemical compounds which are composed of an alkali metal cation, i.e. on of lithium (Li), sodium (Na), potassium (K), rubidium (Rb), caesium (Cs), and the hydroxide anion (HO—). In particular, the alkali metal cation is K or Na. More preferably, the base is NaOH. Most preferably, the first layer is basified by adding 10% NaOH for obtaining a pH of about 9 to 10 before step (iii).

The method of the present invention further comprises a step (iii) of contacting the optionally basified first layer obtained and in step (ii) with a third separation solvent for forming a third layer, which third separation solvent comprises a halogenated hydrocarbon. The third layer in particular comprises the main part of the third separation solvent and the at least one phenanthroindolizidine alkaloid.

The third separation solvent is added to the first layer preferably accompanied by shaking for forming the third layer.

The term "halogenated hydrocarbon" as used herein refers to a hydrocarbon, preferably an alkane, which hydrocarbon has at least one hydrogen atom substituted with a halogen atom. Preferably, the halogenated hydrocarbon in the first extracting solvent is a hydrocarbon, preferably a branched or straight chain alkane, which hydrocarbon has 1 to 4 carbon atoms and wherein at least one hydrogen atom is substituted with a halogen selected from Br, Cl, or F, in particular from Cl. Preferably, the halogenated hydrocarbon is an alkane with 1 to 2 carbon atoms in which at least one hydrogen atom is substituted with a Cl atom, in particular selected from methyl chloride, dichloromethane or chloroform. Most preferably, the halogenated hydrocarbon in the third separation solvent is chloroform. In further preferred embodiments of the present invention, the third separation solvent essentially consists of chloroform.

The method of the present invention further comprises a step (iv) of subjecting the third layer to at least a first chromatographic separation step, preferably carried out with liquid column chromatography including separating by means of fragmentation.

Preferably, step (iv) further comprises a step of removing the solvent portion of the third layer, i.e. in particular the third separation solvent, before carrying out the first chromatographic separation step. The solvent portion is preferably removed by means of evaporation in vacuum.

In embodiments of the present invention, step (iv) comprises a single, i.e. only a first chromatographic separation step. In further embodiments of the present invention, a first and a second chromatographic separation step are carried out in step (iv) and in still further embodiments of the present invention, a first, a second and a third separation step is carried out in step (iv). In further embodiments of the present invention, at least a first, a second, a third and a fourth chromatographic separation step is carried out.

The first chromatographic separation step may be sufficient and, thus, step (iv) consists of a single chromatographic separation step in embodiments, in which a phenanthroindolizidine alkaloid having Formula (III) given above with $R_1$ being H, $R_2$ being $OCH_3$, $R_3$ being $OCH_3$ and $R_4$ being β-OH (compound (18)) is isolated.

The first and the second chromatographic separation step are preferably carried out in step (iv) for isolating a phenanthroindolizidine alkaloid selected from a compound:
  having Formula (III) given above, wherein $R_1$ is OH, $R_2$ is $OCH_3$, $R_3$ is OH and $R_4$ is H (compound (4));
  having Formula (III), wherein $R_1$ is OH, $R_2$ is $OCH_3$, $R_3$ is OH and $R_4$ is α-OH (compound (5));
  having Formula (III), wherein $R_1$ is H, $R_2$ is $OCH_3$, $R_3$ is OH and $R_4$ is α-OH (compound (14));
  or a compound having Formula (III), wherein $R_1$ is $OCH_3$, $R_2$ is $OCH_3$, $R_3$ is $OCH_3$ and $R_4$ is H (compound (19)).

At least the first, the second and the third chromatographic separation step are preferably carried out in step (iv) for isolating a phenanthroindolizidine alkaloid selected from a compound:
  having Formula (I) given above, wherein $R_1$ is $OCH_3$ (compound (2));
  having Formula (II) given above (compound (3));
  having Formula (III) given above, wherein $R_1$ is H, $R_2$ is OH, $R_3$ is OH and $R_4$ is α-OH (compound (13));

having Formula (III), wherein $R_1$ is H, $R_2$ is $OCH_3$, $R_3$ is $OCH_3$ and $R_4$ is H (compound (20));
having Formula (III), wherein $R_1$ is H, $R_2$ is $OCH_3$, $R_3$ is $OCH_3$ and $R_4$ is α-OH (compound (21));
having Formula (IV) given above, wherein $R_1$ is OH, $R_2$ is $OCH_3$, $R_3$ is $OCH_3$ and $R_4$ is β-OH (compound (8));
having Formula (IV), wherein $R_1$ is $OCH_3$, $R_2$ is $OCH_3$, $R_3$ is $OCH_3$ and $R_4$ is α-OH (compound (10));
having Formula (IV), wherein $R_1$ is $OCH_3$, $R_2$ is $OCH_3$, $R_3$ is $OCH_3$ and $R_4$ is H (compound (11));
having Formula (IV), wherein $R_1$ is H, $R_2$ is $OCH_3$, $R_3$ is $OCH_3$ and $R_4$ is H (compound (12));
having Formula (VI) given above (compound (9));
having Formula (VII) given above (compound (16));
having Formula (VIII) given above (compound (17));
or a compound having Formula (IX) given above (compound (22)).

At least the first, the second, the third and the fourth chromatographic separation step are preferably carried out in step (iv) for isolating a phenanthroindolizidine alkaloid selected from a compound:
having Formula (I) given above, wherein $R_1$ is OH (compound (1));
having Formula (III) given above, wherein $R_1$ is H, $R_2$ is OH, $R_3$ is $OCH_3$ and $R_4$ is α-OH (compound (15));
having Formula (IV) given above, wherein $R_1$ is H, $R_2$ is OH, $R_3$ is OH and $R_4$ is β-OH (compound (6));
or a compound having Formula (V) given above (compound (7)).

Chromatographic separation steps in step (iv) are preferably carried out with liquid chromatography including column chromatography and can be carried out as classical (low pressure) column chromatography usually operating with a low pressure up to about 0.5 MPa, high-performance liquid chromatography (HPLC) usually with operational pressures up to 5 MPa or higher. HPLC can be carried out as semi-preparative or preparative HPLC.

Preferably, the first chromatographic separation step is selected from classical (low pressure) column chromatography, in particular with a polyaromatic adsorbent resin, preferably with a styrene-divinylbenzene polymer resin as stationary phase like MCI CH20P gel.

The optional further chromatographic separation steps, in particular the second, the third and the fourth chromatographic separation steps and any further chromatographic separation steps preferably comprise liquid chromatography, which may be carried out as classical column chromatography or HPLC. The stationary phase is preferably selected from unmodified silica gel (further referenced as "silica gel") or a reverse phase, in particular a C18 reverse phase like octadecylsilyl groups.

Classical column chromatography can be carried out with unmodified silica gel preferably with a particle size of about 40 μm to about 63 μm. Alternatively, classical column chromatography can be carried out with a reverse phase, namely a stationary phase having alkyl chains covalently bonded to a solid support leading to a hydrophobic stationary phase, in particular including C18 phases, i.e. with octadecyl-chains (C18 chains) in particular with a particle size of about 55 μm to 105 μm and preferably with a pore size of about 125 Å.

HPLC can be carried out with a reverse phase as stationary phase, in particular a C18 reverse phase with a particle size of about 5 μm and preferably with column dimensions of about 250×10 mm.

In embodiments, in which the second chromatographic separation step is carried out in step (iv), the second chromatographic separation step is preferably carried out by means of classical (low pressure) column chromatography with unmodified silica gel as stationary phase. In embodiments, in which the third chromatographic separation step is carried out in step (iv), the third chromatographic separation step is preferably carried out by means of classical (low pressure) column chromatography with a C18 reverse phase as stationary phase or by means of a HPLC with a C18 reverse phase as stationary phase. In embodiments, in which the fourth or even more chromatographic separation steps are carried out in step (iv), the fourth and any further chromatographic separation step is preferably carried out by means of a HPLC with a C18 reverse phase as stationary phase.

The first chromatographic separation step is preferably carried out by means of classical column chromatography and preferably includes fractionating the third layer and its components, respectively, to obtain several fractions, in particular at least 10 fractions, more preferably at least 15 fractions, i.e. including collecting individual eluate fractions rich in the at least one phenanthroindolizidine alkaloid to be isolated. The first chromatographic separation step is preferably carried out as gradient elution, i.e. with a gradient of eluting solvents.

More preferably, the first chromatographic separation step is carried out with a styrene-divinylbenzene polymer resin as stationary phase like MCI CH20P gel and preferably with eluting solvents selected from at least three of $C_1$ to $C_3$ aliphatic alcohol, a $C_2$ to $C_4$ ketone, water, a $C_2$ to $C_6$ aliphatic amine, preferably at least three of methanol, acetone, water and/or diethyl amine.

The term "aliphatic amine" refers to an alkylamine in particular having a formula $NH_yB_x$, wherein x and y are selected from among x=1, y=2 and x=2, y=1, preferably x=2, y=1. Each B is a straight chain or branched C1-C3 alkyl, i.e. the number of carbon atoms in each B is 1 to 3 and preferably 2.

More preferably, methanol/water/diethyl amine and subsequently acetone/methanol/diethyl amine are used as elution solvents. Most preferably, the following elution solvents and gradients are subsequently applied:
a) methanol/water/diethyl amine with a gradient of 7:3:0.05 to 10:0:0.05, and subsequently
b) acetone/methanol/diethyl amine with a gradient of 1:9:0.05 to 6:4:0.05.

Preferably, by subjecting the third layer in particular after removing the solvent portion to a styrene-divinylbenzene polymer resin as stationary phase and eluting with elution solvents a) and b) phenanthroindolizidine alkaloid having Formula (III) with $R_1$ being H, $R_2$ being $OCH_3$, $R_3$ being $OCH_3$ and $R_4$ being β-OH (compound (18)) can be isolated, and additionally at least 10 fractions are selected, more preferably about 15 fractions are selected and most preferably 15 fractions (i.e. fractions 1 to 15, further referenced as "fraction no. XX"). The fractions are preferably selected based on a thin layer chromatography (TLC) monitoring which is usual practice in the art, i.e. the number and size of each fraction is determined by the specific composition and changes in the composition as well as the presence of alkaloids. I.e. a change in the composition confirmed with TLC means next fraction. For example, when a new compound shows up in the eluted part compared with the already eluted parts confirmed with TLC, this represents a new fraction until there is a change in the composition, e.g. said new compound is no longer eluted. The presence of alkaloids can be verified with usual and well-known reagents. TLC is preferably carried out with silica gel, in particular silica gel 60 $F_{254}$.

For isolating the phenanthroindolizidine alkaloid of Formula (IV) given above with $R_1$ being H, $R_2$ being OH, $R_3$ being OH and $R_4$ being β-OH (compound (6)) and/or of Formula (V) (compound (7)) given above:
- 15 fractions are obtained as defined above, wherein fraction no. 3 is preferably subjected to a classical column chromatography with silica gel and with eluting solvents comprising a $C_1$ to $C_2$ halogenated hydrocarbon, a $C_1$ to $C_3$ aliphatic alcohol and a $C_2$ to $C_6$ aliphatic amine, most preferably with chloroform/methanol/diethyl amine and a gradient of 10:0:0.05 to 3:7:0.05 for obtaining about 17 subfractions (i.e. subfractions no. 3-1 to 3-17) as determined by TLC monitoring; and
- subjecting subfraction no. 3-15 to classical column chromatography with a C18 reverse phase with eluting solvents comprising a $C_1$ to $C_3$ aliphatic alcohol and water, in particular methanol/water with a gradient of 1:1 to 4:1 and subsequently to HPLC.

For isolating the phenanthroindolizidine alkaloid of Formula (III) given above with $R_1$ is OH, $R_2$ is $OCH_3$, $R_3$ is OH and $R_4$ is α-OH (compound (5)) and/or of Formula (III) given above with $R_1$ being H, $R_2$ being OH, $R_3$ being OH and $R_4$ being α-OH (compound (13)):
- fraction no. 4 is preferably subjected to a classical column chromatography with silica gel and with eluting solvents comprising a $C_1$ to $C_2$ halogenated hydrocarbon, a $C_1$ to $C_3$ aliphatic alcohol and a $C_2$ to $C_6$ aliphatic amine, most preferably with chloroform/methanol/diethyl amine and a gradient of 10:0:0.05 to 3:1:0.05 for obtaining phenanthroindolizidine alkaloid of Formula (III) given above with $R_1$ is OH, $R_2$ is $OCH_3$, $R_3$ is OH and $R_4$ is α-OH (compound (5)) and 6 subfractions (subfractions no. 4-1 to 4-6) based on the TCL behavior, and
- subjecting subfraction no. 4-6 to classical column chromatography with a C18 reverse phase with eluting solvents comprising a $C_1$ to $C_3$ aliphatic alcohol and water, in particular methanol/water 1:1 for obtaining a phenanthroindolizidine alkaloid of Formula (III) given above with $R_1$ being H, $R_2$ being OH, $R_3$ being OH and $R_4$ being α-OH (compound (13)).

For isolating the phenanthroindolizidine alkaloid of Formula (III) given above with $R_1$ is OH, $R_2$ is $OCH_3$, $R_3$ is OH and $R_4$ is H (compound (4)):
- fraction no. 5 is preferably subjected to a classical column chromatography with silica gel and with eluting solvents comprising a $C_1$ to $C_2$ halogenated hydrocarbon, a $C_1$ to $C_3$ aliphatic alcohol and a $C_2$ to $C_6$ aliphatic amine, most preferably with chloroform/methanol/diethyl amine and a gradient of 10:0:0.05 to 5:2:0.05.

For isolating at least one of the phenanthroindolizidine alkaloids of Formula (I) with $R_1$ being OH (compound (1)), of Formula (III) with $R_1$ being H, $R_2$ being $OCH_3$, $R_3$ being OH and $R_4$ being α-OH (compound (14)), of Formula (III) with $R_1$ being H, $R_2$ being OH, $R_3$ being $OCH_3$ and $R_4$ being α-OH (compound (15)) and/or of Formula (VII) (compound (16)):
- fraction no. 8 is preferably subjected to a classical column chromatography with silica gel and with eluting solvents comprising a $C_1$ to $C_2$ halogenated hydrocarbon, a $C_1$ to $C_3$ aliphatic alcohol and a $C_2$ to $C_6$ aliphatic amine, most preferably with chloroform/methanol/diethyl amine and a gradient of 10:0:0.05 to 7:3:0.05 for obtaining phenanthroindolizidine alkaloid of Formula (III) with $R_1$ being H, $R_2$ being $OCH_3$, $R_3$ being OH and $R_4$ being α-OH (compound (14)) and 24 subfractions (subfractions no. 8-1 to 8-24) determined by TLC monitoring;
- subjecting subfraction no. 8-15 to classical column chromatography with a C18 reverse phase with eluting solvents comprising a $C_1$ to $C_3$ aliphatic alcohol and water, in particular methanol/water 1:1 and subsequently to HPLC for obtaining a phenanthroindolizidine alkaloid of Formula (I) with $R_1$ being OH (compound (1));
- subjecting subfraction no. 8-16 to classical column chromatography with a C18 reverse phase with eluting solvents comprising a $C_1$ to $C_3$ aliphatic alcohol and water, in particular methanol/water 7:3 and subsequently to HPLC for obtaining a phenanthroindolizidine alkaloid of Formula (III) with $R_1$ being H, $R_2$ being OH, $R_3$ being $OCH_3$ and $R_4$ being α-OH (compound (15));
- subjecting subfraction no. 8-23 to classical column chromatography with a C18 reverse phase with eluting solvents comprising a $C_1$ to $C_3$ aliphatic alcohol and water, in particular methanol/water with a gradient 2:3 to 3:2 for obtaining a phenanthroindolizidine alkaloid of Formula (VII) (compound (16)).

For isolating the phenanthroindolizidine alkaloid of Formula (IV) given above with $R_1$ being OH, $R_2$ being $OCH_3$, $R_3$ being $OCH_3$ and $R_4$ being β-OH (compound (8)):
- fraction no. 9 is preferably subjected to a classical column chromatography with silica gel and with eluting solvents comprising a $C_1$ to $C_2$ halogenated hydrocarbon, a $C_1$ to $C_3$ aliphatic alcohol and a $C_2$ to $C_6$ aliphatic amine, most preferably with chloroform/methanol/diethyl amine and a gradient of 10:0:0.05 to 5:5:0.05 and subsequently to repeated HPLC.

For isolating the phenanthroindolizidine alkaloid of Formula (III) given above with $R_1$ being $OCH_3$, $R_2$ being $OCH_3$, $R_3$ being $OCH_3$ and $R_4$ being H (compound (19)):
- fraction no. 11 is preferably subjected to a classical column chromatography with silica gel and with eluting solvents comprising a $C_1$ to $C_2$ halogenated hydrocarbon, a $C_1$ to $C_3$ aliphatic alcohol and a $C_2$ to $C_6$ aliphatic amine, most preferably with chloroform/methanol/diethyl amine and a gradient of 10:0:0.05 to 4:6:0.05.

For isolating the phenanthroindolizidine alkaloid of Formula (VI) (compound (9)):
- fraction no. 12 is preferably subjected to a classical column chromatography with silica gel and with eluting solvents comprising a $C_1$ to $C_2$ halogenated hydrocarbon, a $C_1$ to $C_3$ aliphatic alcohol and a $C_2$ to $C_6$ aliphatic amine, most preferably with chloroform/methanol/diethyl amine and a gradient of 10:0:0.05 to 4:6:0.05 and subsequently to HPLC.

For isolating the phenanthroindolizidine alkaloid of Formula (I) with $R_1$ being $OCH_3$ (compound (2)), of Formula (II) (compound (3)), of Formula (III) with $R_1$ being H, $R_2$ being $OCH_3$, $R_3$ being $OCH_3$ and $R_4$ being H (compound (20)), of Formula (III) with $R_1$ being H, $R_2$ being $OCH_3$, $R_3$ being $OCH_3$ and $R_4$ being α-OH (compound (21)), of Formula (IV) with $R_1$ being $OCH_3$, $R_2$ being $OCH_3$, $R_3$ being $OCH_3$ and $R_4$ being α-OH (compound (10)); of Formula (IV) with $R_1$ being $OCH_3$, $R_2$ being $OCH_3$, $R_3$ being $OCH_3$ and $R_4$ being H (compound (11)), of Formula (IV) with $R_1$ being H, $R_2$ being $OCH_3$, $R_3$ being $OCH_3$ and $R_4$ being H (compound (12)), of Formula (VIII) (compound (17)) and/or of Formula (IX) (compound (22)):

fraction no. 13 is preferably subjected to a classical column chromatography with silica gel and with eluting solvents comprising a $C_1$ to $C_2$ halogenated hydrocarbon, a $C_1$ to $C_3$ aliphatic alcohol and a $C_2$ to $C_6$ aliphatic amine, most preferably with chloroform/methanol/diethyl amine and a gradient of 10:0:0.05 to 4:6:0.05 and subsequently to HPLC.

In another aspect, the present invention refers to a phenanthroindolizidine alkaloid, namely a compound selected from the group consisting of:

a compound having Formula (I):

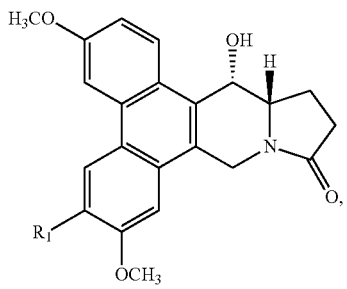

Formula (I)

wherein $R_1$ is OH;

a compound having Formula (II):

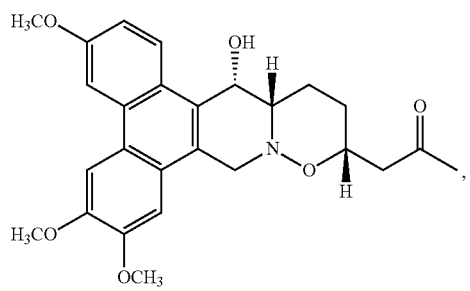

Formula (II)

a compound having Formula (III):

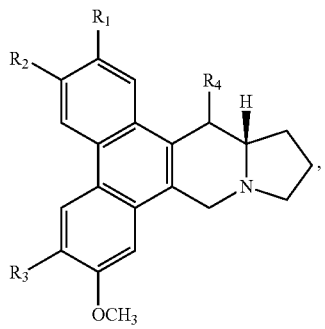

Formula (III)

wherein $R_1$ is OH, $R_2$ is $OCH_3$, $R_3$ is OH and $R_4$ is H;
a compound having Formula (III) above, wherein $R_1$ is OH, $R_2$ is $OCH_3$, $R_3$ is OH and $R_4$ is α-OH;

a compound having Formula (IV):

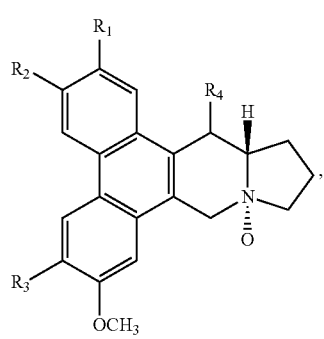

Formula (IV)

wherein $R_1$ is H, $R_2$ is OH, $R_3$ is OH and $R_4$ is β-OH;
a compound having Formula (IV) above, wherein $R_1$ is OH, $R_2$ is $OCH_3$, $R_3$ is $OCH_3$ and $R_4$ is β-OH;
a compound having Formula (IV) above, wherein $R_1$ is $OCH_3$, $R_2$ is $OCH_3$, $R_3$ is $OCH_3$ and $R_4$ is α-OH;
a compound having Formula (IV) above, wherein $R_1$ is $OCH_3$, $R_2$ is $OCH_3$, $R_3$ is $OCH_3$ and $R_4$ is H;
a compound having Formula (IV) above, wherein $R_1$ is H, $R_2$ is $OCH_3$, $R_3$ is $OCH_3$ and $R_4$ is H;
a compound having Formula (V):

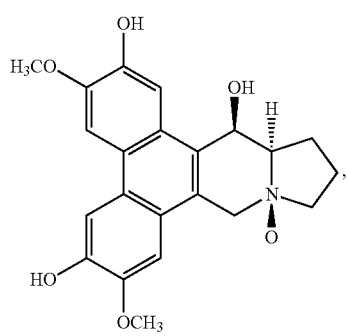

Formula (V)

and a compound having Formula (VI):

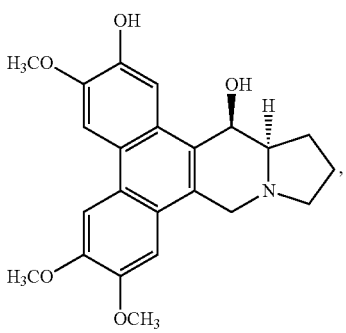

Formula (VI)

which can be isolated from *Tylophora atrofolliculata* by the method described above.

Further in accordance with the present invention is a composition, preferably a pharmaceutical composition, comprising and in particular essentially consisting of:
at least one, in particular one phenanthroindolizidine alkaloid, in particular as pharmaceutically effective ingredient, isolated from *Tylophora atrofolliculata* according to the method described above, and at least one pharmaceutically tolerable excipient such as one or more of a diluent, a filler, a binder, a disintegrant, a lubricant, a coloring agent, a surfactant and a preservative.

The phenanthroindolizidine alkaloid comprised in the composition, in particular in the pharmaceutical composition, is preferably selected from at least one, more preferably one of:

a compound having Formula (I):

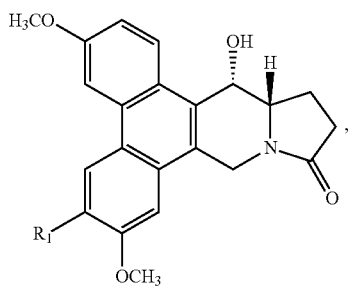

Formula (I)

wherein $R_1$ is OH;

a compound having Formula (II):

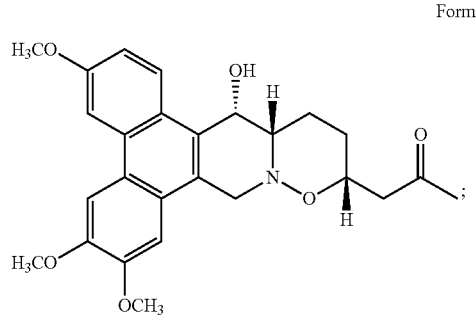

Formula (II)

a compound having Formula (III):

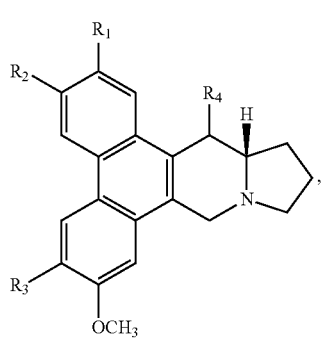

Formula (III)

wherein $R_1$ is OH, $R_2$ is $OCH_3$, $R_3$ is OH and $R_4$ is H;
a compound having Formula (III) above, wherein $R_1$ is OH, $R_2$ is $OCH_3$, $R_3$ is OH and $R_4$ is α-OH;

a compound having Formula (IV):

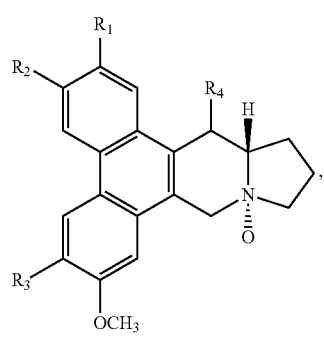

Formula (IV)

wherein $R_1$ is H, $R_2$ is OH, $R_3$ is OH and $R_4$ is β-OH;
a compound having Formula (IV) above, wherein $R_1$ is OH, $R_2$ is $OCH_3$, $R_3$ is $OCH_3$ and $R_4$ is β-OH;
a compound having Formula (IV) above, wherein $R_1$ is $OCH_3$, $R_2$ is $OCH_3$, $R_3$ is $OCH_3$ and $R_4$ is α-OH;
a compound having Formula (IV) above, wherein $R_1$ is $OCH_3$, $R_2$ is $OCH_3$, $R_3$ is $OCH_3$ and $R_4$ is H;
a compound having Formula (IV) above, wherein $R_1$ is H, $R_2$ is $OCH_3$, $R_3$ is $OCH_3$ and $R_4$ is H;
a compound having Formula (V):

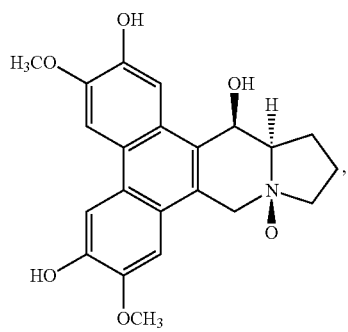

Formula (V)

or a compound having Formula (VI):

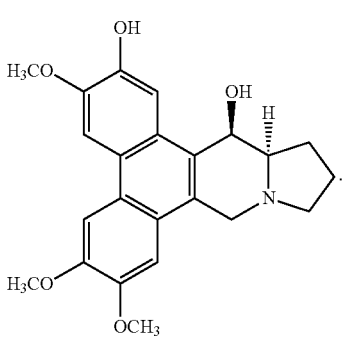

Formula (VI)

In more preferred embodiments of the present invention, the phenanthroindolizidine alkaloid comprised in the composition is one of:

a compound having Formula (III) given above, wherein $R_1$ is OH, $R_2$ is $OCH_3$, $R_3$ is OH and $R_4$ is H;

a compound having Formula (III), wherein $R_1$ is OH, $R_2$ is $OCH_3$, $R_3$ is OH and $R_4$ is α-OH;

a compound having Formula (IV) given above, wherein $R_1$ is H, $R_2$ is OH, $R_3$ is OH and $R_4$ is β-OH;

a compound having Formula (IV), wherein $R_1$ is OH, $R_2$ is $OCH_3$, $R_3$ is $OCH_3$ and $R_4$ is β-OH;

a compound having Formula (IV), wherein $R_1$ is H, $R_2$ is $OCH_3$, $R_3$ is $OCH_3$ and $R_4$ is H;

or a compound having Formula (V) given above.

In most preferred embodiments of the present invention, the phenanthroindolizidine alkaloid comprised in the composition is one of:

a compound having Formula (III) given above, wherein $R_1$ is OH, $R_2$ is $OCH_3$, $R_3$ is OH and $R_4$ is H;

a compound having Formula (III), wherein $R_1$ is OH, $R_2$ is $OCH_3$, $R_3$ is OH and $R_4$ is α-OH;

a compound having Formula (IV) given above, wherein $R_1$ is H, $R_2$ is OH, $R_3$ is OH and $R_4$ is β-OH;

or a compound having Formula (V) given above.

The phenanthroindolizidine alkaloid is contained in the composition, in particular the pharmaceutical composition, preferably in an effective amount, i.e. an amount suitable to treat or prevent a disease in a subject, in particular a human, which also depends on the frequency and number of compositions to be administered. The phenanthroindolizidine alkaloid administered preferably has an $IC_{50}$ regarding the inhibition of HIF-1 which is below 300 nM, more preferably below 100 nM and in particular less than 50 nM such as at most 45 nM. The cancer may be a breast cancer.

The skilled person is able to select suitable pharmaceutically tolerable excipients depending on the form of the pharmaceutical composition and is aware of methods for manufacturing pharmaceutical compositions as well as able to select a suitable method for preparing the pharmaceutical composition depending on the kind of pharmaceutically tolerable excipients and the form of the pharmaceutical composition.

The pharmaceutical composition according to the invention can be present in solid, semisolid or liquid form to be administered by an oral, rectal, topical, parenteral or transdermal or inhalative route to a subject, preferably a human.

The pharmaceutical composition may comprise further pharmaceutical effective ingredients such as therapeutic compounds used for treating cancer. The pharmaceutical composition may be provided in form of a kit comprising the pharmaceutical composition described above and at least one further pharmaceutical composition having another active ingredient for treating cancer such as a cytotoxic ingredient or an angiogenesis inhibitor.

Further in accordance with the present invention is a method of treating a subject suffering from cancer comprising administering an effective amount of at least one phenanthroindolizidine alkaloid, preferably one phenanthroindolizidine alkaloid, isolated from *Tylophora atrofolliculata* according to the method described above to the subject.

In particular, the method comprises administering an affective amount of at least one phenanthroindolizidine alkaloid and preferably one phenanthroindolizidine alkaloid:

having Formula (III):

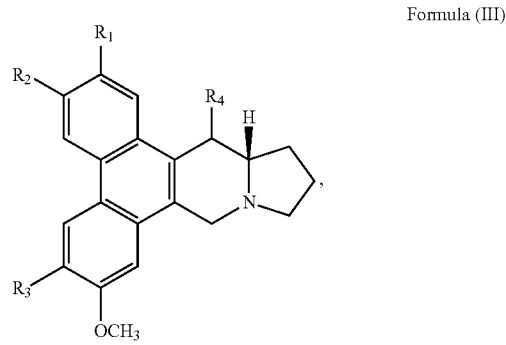

Formula (III)

wherein $R_1$ is OH, $R_2$ is $OCH_3$, $R_3$ is OH and $R_4$ is H;

having Formula (III) above, wherein $R_1$ is OH, $R_2$ is $OCH_3$, $R_3$ is OH and $R_4$ is α-OH;

having Formula (III) above, wherein $R_1$ is H, $R_2$ is OH, $R_3$ is OH and $R_4$ is α-OH;

having Formula (III) above, wherein $R_1$ is H, $R_2$ is $OCH_3$, $R_3$ is OH and $R_4$ is α-OH;

having Formula (III) above, wherein $R_1$ is H, $R_2$ is OH, $R_3$ is $OCH_3$ and $R_4$ is α-OH;

having Formula (III) above, wherein $R_1$ is H, $R_2$ is $OCH_3$, $R_3$ is $OCH_3$ and $R_4$ is β-OH;

having Formula (III) above, wherein $R_1$ is H, $R_2$ is $OCH_3$, $R_3$ is $OCH_3$ and $R_4$ is H;

having Formula (III) above, wherein $R_1$ is H, $R_2$ is $OCH_3$, $R_3$ is $OCH_3$ and $R_4$ is α-OH;

having Formula (IV):

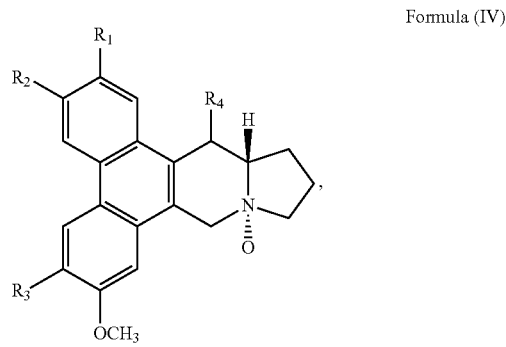

Formula (IV)

wherein $R_1$ is H, $R_2$ is OH, $R_3$ is OH and $R_4$ is β-OH;

having Formula (IV) above, wherein $R_1$ is OH, $R_2$ is $OCH_3$, $R_3$ is $OCH_3$ and $R_4$ is β-OH;

having Formula (IV) above, wherein $R_1$ is H, $R_2$ is $OCH_3$, $R_3$ is $OCH_3$ and $R_4$ is H;

having Formula (V):

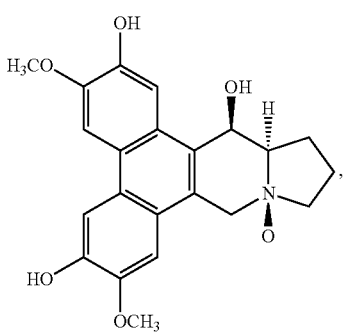

Formula (V)

having Formula (VII):

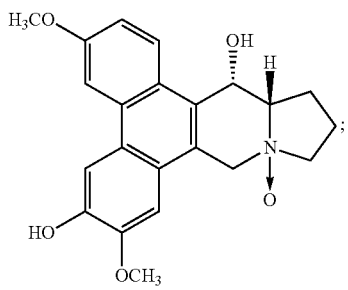

Formula (VII)

or having Formula (VIII):

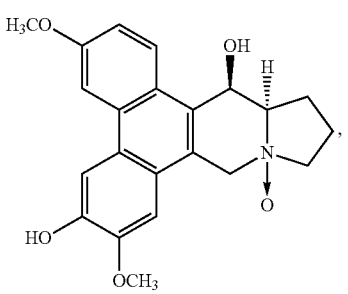

Formula (VIII)

which can be isolated from *Tylophora atrofolliculata* by the method described above.

Most preferably, the method comprises administering an affective amount of a phenanthroindolizidine alkaloid:
  having Formula (III) given above, wherein $R_1$ is OH, $R_2$ is $OCH_3$, $R_3$ is OH and $R_4$ is H;
  having Formula (III), wherein $R_1$ is OH, $R_2$ is $OCH_3$, $R_3$ is OH and $R_4$ is α-OH;
  having Formula (IV) given above, wherein $R_1$ is H, $R_2$ is OH, $R_3$ is OH and $R_4$ is β-OH;
  having Formula (IV), wherein $R_1$ is OH, $R_2$ is $OCH_3$, $R_3$ is $OCH_3$ and $R_4$ is β-OH;
  having Formula (IV), wherein $R_1$ is H, $R_2$ is $OCH_3$, $R_3$ is $OCH_3$ and $R_4$ is H;
  having Formula (V) given above.

The subject is an animal or human, preferably it is a mammal and most preferably a human. The expression "effective amount" generally denotes an amount sufficient to produce therapeutically desirable results, wherein the exact nature of the result varies depending on the specific disorder which is treated. When the disorder is cancer, the result is usually an inhibition or suppression of the proliferation of the cancer cells, a reduction of cancerous cells or the amelioration of symptoms related to the cancer cells.

The effective amount of the phenanthroindolizidine alkaloid isolated from *Tylophora atrofolliculata* may depend on the $IC_{50}$, the species, body weight, age and individual conditions of the subject and can be determined by standard procedures such as with cell cultures or experimental animals. The phenanthroindolizidine alkaloid preferably has an $IC_{50}$ regarding the inhibition of HIF-1 which is below 300 nM, more preferably below 100 nM and in particular less than 50 nM such as at most 45 nM. The cancer may be a breast cancer.

Another aspect relates to a method of treating a subject suffering from cancer comprising:
  isolating at least one and preferably one phenanthroindolizidine alkaloid from *Tylophora atrofolliculata* by the method described above, in particular a phenanthroindolizidine alkaloid:
  having Formula (III):

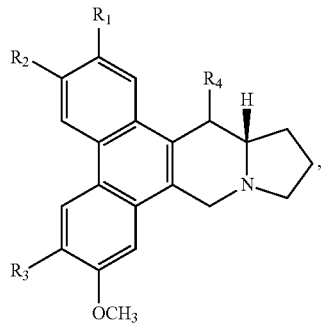

Formula (III)

wherein $R_1$ is OH, $R_2$ is $OCH_3$, $R_3$ is OH and $R_4$ is H;
  having Formula (III) above, wherein $R_1$ is OH, $R_2$ is $OCH_3$, $R_3$ is OH and $R_4$ is α-OH;
  having Formula (IV):

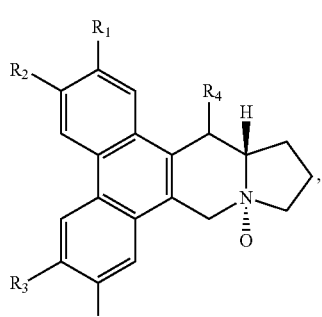

Formula (IV)

wherein $R_1$ is H, $R_2$ is OH, $R_3$ is OH and $R_4$ is β-OH;
  having Formula (IV) above, wherein $R_1$ is OH, $R_2$ is $OCH_3$, $R_3$ is $OCH_3$ and $R_4$ is β-OH;
  having Formula (IV) above, wherein $R_1$ is H, $R_2$ is $OCH_3$, $R_3$ is $OCH_3$ and $R_4$ is H;

or having Formula (V):

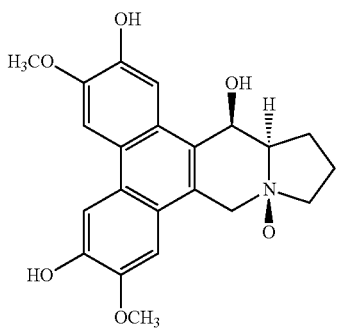

Formula (V)

formulating the at least one phenanthroindolizidine alkaloid into a pharmaceutically composition; and administering said pharmaceutical composition to a subject suffering from cancer. The subject is preferably a human. The cancer is in particular breast cancer.

Further in accordance with the present invention is an at least one phenanthroindolizidine alkaloid isolated from *Tylophora atrofolliculata* with the method described above for use in the treatment of cancer like breast cancer and the use of the at least one phenanthroindolizidine alkaloid isolated from *Tylophora atrofolliculata* with the method described above for preparing a medicament for the treatment of cancer like breast cancer. The phenanthroindolizidine alkaloid in particular is at least one and preferably one of:

a compound having Formula (III) given above, wherein $R_1$ is OH, $R_2$ is $OCH_3$, $R_3$ is OH and $R_4$ is H;

a compound having Formula (III), wherein $R_1$ is OH, $R_2$ is $OCH_3$, $R_3$ is OH and $R_4$ is α-OH;

a compound having Formula (IV) given above, wherein $R_1$ is H, $R_2$ is OH, $R_3$ is OH and $R_4$ is β-OH;

a compound having Formula (IV), wherein $R_1$ is OH, $R_2$ is $OCH_3$, $R_3$ is $OCH_3$ and $R_4$ is β-OH;

a compound having Formula (IV), wherein $R_1$ is H, $R_2$ is $OCH_3$, $R_3$ is $OCH_3$ and $R_4$ is H;

or a compound having Formula (V) given above.

In most preferred embodiments of the present invention, the phenanthroindolizidine alkaloid is one of:

a compound having Formula (III) given above, wherein $R_1$ is OH, $R_2$ is $OCH_3$, $R_3$ is OH and $R_4$ is H;

a compound having Formula (III), wherein $R_1$ is OH, $R_2$ is $OCH_3$, $R_3$ is OH and $R_4$ is α-OH;

a compound having Formula (IV) given above, wherein $R_1$ is H, $R_2$ is OH, $R_3$ is OH and $R_4$ is β-OH;

or a compound having Formula (V) given above.

Another aspect concerns a method of treating a subject suffering from cancer such as breast cancer comprising administering at least one and preferably one phenanthroindolizidine alkaloid isolated from *Tylophora atrofolliculata* with the method described above in particular one of a phenanthroindolizidine alkaloid:

having Formula (III) given above, wherein $R_1$ is OH, $R_2$ is $OCH_3$, $R_3$ is OH and $R_4$ is H;

having Formula (III), wherein $R_1$ is OH, $R_2$ is $OCH_3$, $R_3$ is OH and $R_4$ is α-OH;

having Formula (IV) given above, wherein $R_1$ is H, $R_2$ is OH, $R_3$ is OH and $R_4$ is β-OH;

having Formula (IV), wherein $R_1$ is OH, $R_2$ is $OCH_3$, $R_3$ is $OCH_3$ and $R_4$ is β-OH;

having Formula (IV), wherein $R_1$ is H, $R_2$ is $OCH_3$, $R_3$ is $OCH_3$ and $R_4$ is H;

or having Formula (V) given above, in combination with radiotherapy in particular with X-rays and/or in combination with chemotherapy with further active ingredients for treating cancer, in particular cytotoxic drugs or angiogenesis inhibitors. The expression "in combination with" means a simultaneous or sequential administration or application. In an embodiment of the present invention, the phenanthroindolizidine alkaloid isolated from *Tylophora atrofolliculata* is administered in combination with radiotherapy, wherein the phenanthroindolizidine alkaloid is administered either before or after each radiation, preferably after each radiation.

In still another aspect, the present invention refers to a method for targeting cancer cells in particular breast cancer cells. Said method comprises the step of contacting a population of cancer cells with at least one and preferably one phenanthroindolizidine alkaloid described above. The concentration of the phenanthroindolizidine alkaloid for contacting the cancer cells is preferably between 3 μM and 300 μM, more preferably between 3 μM and 100 μM.

EXAMPLES

Example 1

Example 1A

Materials Used and Conditions Applied

Optical rotations were determined using a Rudolph Research Analytical Autopol I Autometic polarimeter. CD spectra were measured on a Chirascan Circular Dichroism spectrometer. UV data were recorded using a Beckman DU 800 UV/vis spectrophotometer. IR spectra were performed on a Perkin Elmer Spectrum One Fourier transform infrared spectrometer. HRESIMS were recorded on an Agilent 6230 ESI-TOF mass spectrometer. NMR spectral data were obtained from Bruker Ascend™ 600 spectrometer equipped with a cyro platform. Silica gel (Devisil®, 40~63 micron), MCI CH20P gel (Mitsubishi Chemical Corporation) and ODS (Waters, Preparative C18 125 Å, 55~105 μm) were used for column chromatography. Silica gel plates (Merck, D C Kieselgel 60 $F_{254}$) were used for TLC analysis. High-performance liquid chromatography (HPLC) was carried out on Agilent 1100, Agilent 1200 and Waters 1525-2489 apparatus with a semi-preparative column (Waters, XBridge® Prep C18, 5 μm, 250×10 mm). Solvents for HPLC separation analysis were HPLC grade.

The whole plant of *T. atrofolliculata* was collected in Guangxi province, China in 2012 and identified by Dr. Zhifeng Zhang (Faculty of Chinese Medicine, Macau University of Science and Technology). A voucher specimen (No. MUST-TA201302) was deposited at State Key Laboratory of Quality Research in Chinese Medicine, Macau University of Science and Technology.

Example 1B

Isolation of Phenanthroindolizidine Alkaloids from *T. Atrofolliculata*

The whole plant of *T. atrofolliculata* (5.5 kg) was refluxed with methanol for three times to afford a crude extract, namely with amounts of 55 L, 44 L and 33 L of methanol subsequently. Totally 8 h were spent for the solvent extraction, which has been carried out for three times following the order of 4 h, 2 h, and 2 h subsequently. The crude extract after methanol evaporation under reduced pressure was suspended in water as first separation solvent then adjusted to pH 1~2 by adding hydrochloric acid. After being partitioned with ethyl acetate as second separation solvent, the acidic aqueous phase as first layer was basified with 10% sodium hydroxide to pH 9~10 then extracted with chloroform as third separation solvent to afford the third layer with the crude alkaloids (12.6 g).

The third layer after evaporation of chloroform in vacuum was chromatographed over silica gel rendering thirteen fractions, which were further separated through repeated column chromatography (silica gel, ODS, HPLC) to afford twenty-two phenanthroindolizidine alkaloids (compounds (1) to (22)).

The crude alkaloid extract was subjected to chromatography on MCI CH20P gel eluting with methanol-H$_2$O-diethyl amine (7:3:0.05~10:0:0.05), followed by acetone-methanol-diethyl amine (1:9:0.05~6:4:0.05) to yield compound (18) (451 mg) and 15 fractions based on the TLC behavior. Fr. 3 was separated by silica gel using chloroform-methanol-diethyl amine (10:0:0.05~3:7:0.05) to give 17 subfractions based on the TLC behavior. Subfr. 3-15 was chromatographed over ODS (methanol-H$_2$O, 1:1~4:1), and then purified by HPLC to give compound (6) (2 mg), compound (7) (1 mg). Fr. 4 was chromatographed on silica gel column eluting with chloroform-methanol-diethyl amine (10:0:0.05~3:1:0.05) to afford compound (5) (14 mg) and (6) subfractions. Subfr. 4-6 was subjected to chromatography on ODS (methanol-H$_2$O, 1:1) to afford compound (13) (6 mg). Fr. 5 was chromatographed on silica gel column eluting with chloroform-methanol-diethyl amine (10:0:0.05~5:2:0.05) to obtain compound (4) (111 mg). Fr. 8 was subjected to separation over silica gel using chloroform-methanol-diethyl amine (10:0:0.05~7:3:0.05) to give compound (14) (267 mg) and 24 subfractions based on the TLC behavior. Subfr. 8-15 was chromatographed on ODS column (methanol-H$_2$O, 1:1) then purified by HPLC to afford compound (1) (3 mg). Subfr. 8-16 was chromatographed on ODS column (methanol-H$_2$O, 7:3) then purified by HPLC to give compound (15) (1 mg). Subfr. 8-23 was purified by ODS column (methanol-H$_2$O, 2:3~3:2) to give compound (16) (191 mg). Fr. 9 was loaded on silica gel column eluting with chloroform-methanol-diethyl amine (10:0:0.05~5:5:0.05), then purified by repeated HPLC to give compound (8) (1 mg). Fr. 11 was separated by silica gel eluting with chloroform-methanol-diethyl amine (10:0:0.05~4:6:0.05) to give compound (19) (8 mg). Fr. 12 was subjected on silica gel eluting with chloroform-methanol-diethyl amine (10:0:0.05~4:6:0.05), then purified by HPLC to give compound (9) (1 mg). Fr. 13 was chromatographed on silica gel eluting with chloroform-methanol-diethyl amine (10:0:0.05~4:6:0.05) then purified by HPLC to give compound (2) (1 mg), compound (3) (1 mg), compound (10) (20 mg), compound (11) (5 mg), compound (12) (2 mg), compound (17) (40 mg), compound (20) (3 mg), compound (21) (6 mg), compound (22) (7 mg).

The chemical structures of compounds 1 and 3 to 12 were elucidated by means of NMR methods including $^1$H-$^1$H COSY, NOESY, HSQC and HMBC experiments, assisted by high-resolution MS and CD spectral analysis.

Figure 1B:
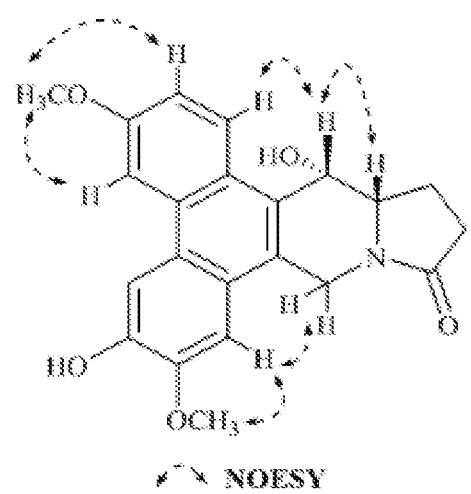

Compound (1) was obtained as white amorphous solid. Its molecular formula was determined as $C_{22}H_{21}NO_5$ by molecular ion at m/z 380.1488 ([M+H]$^+$, calcd 380.1492). The $^1$H NMR data (Table 1) indicated the presence of three aromatic protons with a ABX system [$\delta_H$ 8.14 (d, J=9.0 Hz), 7.89 (d, J=2.4 Hz), 7.25 (dd, J=2.4, 9.0 Hz)], one 1, 2, 4, 5-tetra-substituted benzene ring ($\delta_H$ 8.10, 7.28, each s), two methoxyl groups ($\delta_H$ 3.98, 4.02, each s), two methylene doublets [$\delta_H$ 5.17 (d, J=17.4 Hz), 4.51 (d, J=17.4 Hz)], four methylene multiplets ($\delta_H$ 2.44, 2.37, 2.36, 2.19, each m), one nitrogenated methine ($\delta_H$ 3.91, m), one oxygenated methine ($\delta_H$ 5.09, dd, J=2.4, 7.2 Hz) and one hydroxyl group ($\delta_H$ 5.41, d, J=7.2 Hz). The $^{13}$C NMR spectrum (Table 2) revealed twenty-two carbon resonances, corresponding to fourteen aromatic (three oxygenated and six quaternary carbons), three methylene (one nitrogenated methylene group), two methine (one oxygenated and one nitrogenated methine group), two methoxyl and one carbonyl carbons. The NMR data of compound (1) (see Tables 1 and 2) closely resembled those of compound (14) (Zhen, Y. et al., Acta Bot. Sin., 2002, 44, 349-353) except for the presence of an additional carbonyl group ($\delta_c$ 173.5) instead of the C-11 methylene group, which was confirmed by HMBC correlations of H-9, H-12, H-13 and H-13a with C-11 (FIGS. 1A and 1B). The methoxyl groups were determined to be placed at C-3 and C-7 on the basis of HMBC correlations of OCH$_3$-3 with C-3, OCH$_3$-7 with C-7 as well as the NOESY correlations OCH$_3$-3/H-2 and H-4, OCH$_3$-7/H-8 (FIGS. 1A and 1B). The hydroxyl group was thus placed at C-6 due to the carbon resonance at $\delta_c$ 146.9 (Table 2). Relative configuration of compound (1) was assigned on the basis of the coupling constant and NOE correlation. The small coupling constant (J=2.4 Hz) between H-13a and H-14 and the strong NOE correlation H-13a/H-14 prompted the cis orientation for both protons (FIGS. 1A and 1B). Absolute configuration of compound (1) was determined through its CD spectrum, where the negative Cotton effect was observed at 253 nM, suggesting S configuration at C-13a (Damu, A. G. et al., Planta Med., 2009, 75, 1152-1156, Zhen, Y. et al., Acta Bot. Sin., 2002, 44, 349-353, Stærk, D. et al., J. Nat. Prod., 2000, 63, 1584-1586, S. F, J. F. Mi et al., Acta Pharm. Sin. B, 27, 197-203). Thus, compound (1) was identified as 11-keto-tylophorinidine (i.e. having Formula (I) with R$_1$ being OH).

11-keto-tylophorinidine (compound (1)). White powder; $[\alpha]_D^{25}$ −66 (c 0.38 CHCl$_3$-MeOH 3:1); UV (CHCl$_3$) $\lambda_{max}$ (log ∈) 250 (4.56, sh), 259 (4.65), 286 (4.40), 313 (3.93) nm; CD (MeOH) 204 ($\Delta\epsilon$-6.93), 253 ($\Delta\epsilon$-1.59) nm; $^1$H and $^{13}$C NMR data, see Tables 1 and 2; HRESIMS m/z 380.1488 [M+H]$^+$ (calcd for $C_{22}H_{21}NO_5$, 380.1492).

Figure 2A:
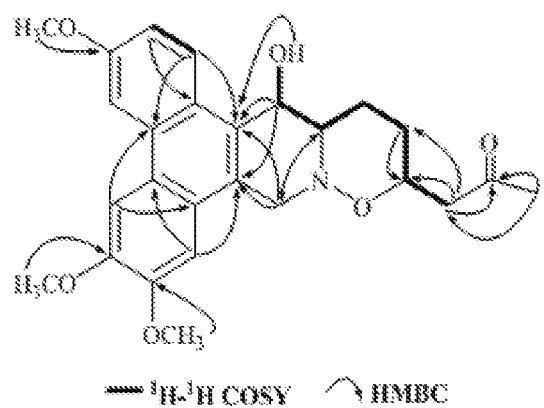
FIG. 2A and FIG. 2B show the key correlations observed in $^1$H-$^1$H COSY, HMBC, and NOESY spectra of compound (3), respectively.
Figure 2B:
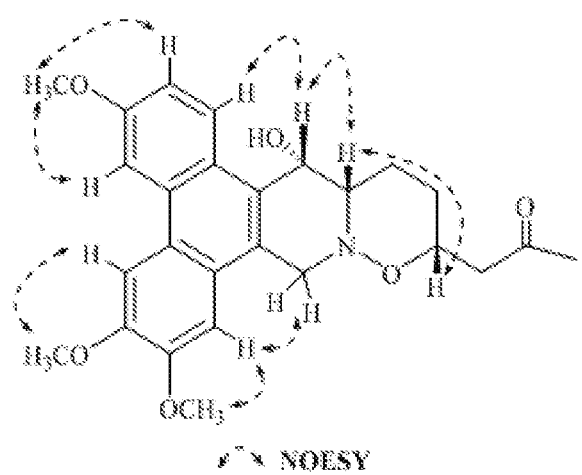

Compound (3) was obtained as white powder. Its molecular formula $C_{26}H_{29}NO_6$ was deduced from HRESIMS peak at m/z 452.2069 ([M+H]$^+$, calcd 452.2068). The $^1$H and $^{13}$C NMR spectra (Table 3) collectively revealed three methoxyl groups, one methyl group, four methylene groups (one nitrogenated), three methine groups (two oxygenated, one nitrogenated), one hydroxyl group and one carbonyl group. The NMR data of compound (3) (Table 3) closely matched those of 14aS, 15S-hydroxyboehmeriasin A (Z. Wang and Q. Wang, Tetrahedron Lett., 2010, 51, 1377-1379) except for an additional oxazine instead of C-11 methylene, and a 2-oxo-propyl group located at C-12. The formation of oxazine was inferred from carbon resonance of C-12 at $\delta_c$ 74.1 (Table 3) (Labaziewicz, H. et al., J. Chem. Soc., 1977, 619-622). The HMBC correlations of H-16 and H-18 with C-17, H-18 with C-16 established the 2-oxopropyl group, which was connected to C-12 based on the HMBC correlation of H-16 with C-12 along with $^1$H-$^1$H COSY correlation H-16/H-12 (FIGS. 2A and 2B). The methoxyl groups were assigned at C-3, C-6, C-7 by means of the HMBC correlations of OCH$_3$-3 with C-3, OCH$_3$-6 with C-6, OCH$_3$-7 with C-7, as well as the NOE correlations OCH$_3$-3/H-2 and H-4, OCH$_3$-6/H-5, OCH$_3$-7/H-8 (FIGS. 2A and 2B). Relative configuration of compound (3) was assigned on the basis of NOE correlations and coupling constant. The strong NOE correlation H-14a/H-15 and the coupling constant (J=6.0 Hz) between H-14a and H-15 indicated that H-15 was cis to H-14a (Cai, X. F. et al., J. Nat. Prod., 2006, 69, 1095-1097). The strong NOE correlation H-12/H-14a suggested the cis position of both protons (FIGS. 2A and 2B). Absolute configuration of compound (3) was assigned through comparing its optical rotation with known compounds. Since 14aS, 15S-hydroxyboehmeriasin A had a specific optical activity of $[\square]_D^{20}$ +57 (c 0.5 CHCl$_3$) (Z. Wang and Q. Wang, Tetrahedron Lett., 2010, 51, 1377-1379). Absolute configuration of compound (3) at H-14a was deduced to be S tentatively on the basis of its positive optical rotation value (Cai, X. F. et al., J. Nat. Prod., 2006, 69, 1095-1097, Z. Wang and Q. Wang, Tetrahedron Lett., 2010, 51, 1377-1379, T. F. Buckley and R. Henry, J. Org. Chem., 1983, 48, 4222-4232). Hence, compound (3) was established as 12S, 14aS, 15S-11-oxa-12-(2-oxopropyl)-hydroxyboehmeriasin A (i.e. having Formula (II)).

12S, 14aS, 15S-11-oxa-12-(2-oxopropyl)-hydroxyboehmeriasin A (compound (3)). White powder; $[\alpha]_D^{23}$ +9 (c 0.1 CHCl$_3$); UV (CHCl$_3$) $\lambda_{max}$ (log ∈) 257 (4.84), 285 (4.54), 310 (4.01) nm; $^1$H and $^{13}$C NMR data, see Table 3; HRES-IMS m/z 452.2069 [M+H]$^+$ (calcd for C$_{26}$H$_{29}$NO$_6$, 452.2068).

Figure 3A:
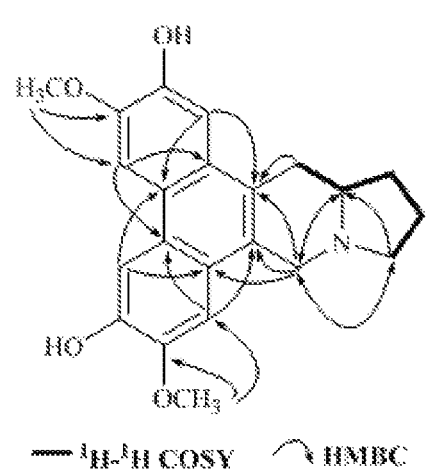
FIG. 3A and FIG. 3B show the key correlations observed in $^1$H-$^1$H COSY, HMBC, and NOESY spectra of compound (4), respectively.
Figure 3B:
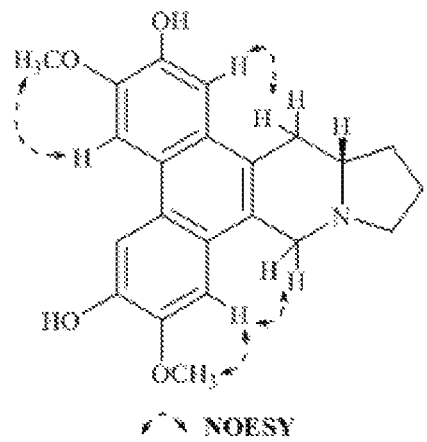

Compound (4) was isolated as white powder. HRESIMS gave a protonated molecule at m/z 366.1692 [M+H]$^+$ (calcd 366.1700 for C$_{22}$H$_{23}$NO$_4$). The $^1$H NMR data (Table 1) indicated the presence of two 1, 2, 4, 5-tetra-substituted benzene rings ($\delta_H$ 7.95, 7.82, 7.25, 7.14, each s), two methoxyl groups ($\delta_H$ 3.93, 3.99, each s), two methylene doublets [$\delta_H$ 4.52 (d, J=15.0 Hz), 3.47 (d, J=15.0 Hz)], eight methylene multiplets ($\delta_H$ 3.30, 3.17, 2.65, 2.31, 2.13, 1.83, 1.82, 1.60, each m), one nitrogenated methine ($\delta_H$ 2.34, m). The $^{13}$C NMR spectra (Table 2) revealed twenty-two carbon resonances, corresponding to fourteen aromatic (four oxygenated and six quaternary carbons), five methylene (two nitrogenated methylene groups), two methoxyl and one nitrogenated methine carbons. All the aforementioned information indicated the presence of phenanthroindolizidine moiety (Huang, X. et al., Planta Med., 2004, 70, 441-445). The two methoxyl groups were determined to be placed at C-3 and C-7 via the strong HMBC correlations of OCH$_3$-3 with C-3, OCH$_3$-7 with C-7, and weak correlations of OCH$_3$-3 with C-4, OCH$_3$-7 with C-8 (FIGS. 3A and 3B). This was further confirmed by the NOESY spectrum, which displayed correlations OCH$_3$-3/H-4 and OCH$_3$-7/H-8 (FIGS. 3A and 3B). The remaining functionalities were designated as two hydroxyl groups and assigned to C-2 and C-6 due to the presence of carbon resonances at $\delta_c$ 146.2 and 146.0 (Table 2). The absolute stereochemistry of compound (4) was inferred from its and CD spectrum. The negative Cotton effect at 257 nM in CD spectrum inferred the S configuration at C-13a (Damu, A. G. et al., Planta Med., 2009, 75, 1152-1156, Zhen, Y. et al., Acta Bot. Sin., 2002, 44, 349-353, Stærk, D. et al., J. Nat. Prod., 2000, 63, 1584-1586). The data described above led to the assignment of the structure of compound (4) as 2-hydroxyl deoxytylophorinidine (i.e. having Formula (III) with R$_1$ being OH, R$_2$ being OCH$_3$, R$_3$ being OH and R$_4$ being H).

2-hydroxyl deoxytylophorinidine (compound (4)). White powder; $[\alpha]_D^{24}$ −156 (c 0.26, CHCl$_3$-MeOH 4:1); UV (MeOH) $\lambda_{max}$ (log ∈) 257 (4.72), 248 (4.57, sh), 291 (4.49), 304 (4.26, sh) nm; IR (KBr): $v_{max}$=2960, 2936, 2831, 1620, 1516, 1465, 1261, 1203, 1155, 1039, 854, 785 cm$^{-1}$; CD (MeOH) 257 (Δε −45.00) nm; $^1$H and $^{13}$C NMR data, see Tables 1 and 2; HRESIMS m/z 366.1692 [M+H]$^+$ (calcd for C$_{22}$H$_{23}$NO$_4$, 366.1700).

Compound (5) was obtained as white powder. Its molecular formula C$_{22}$H$_{23}$NO$_5$ derived from protonated molecular ion peak (m/z 382.1665 [M+H]$^+$, calcd 382.1649). Compound (5) was clearly an analogue of compound (4), as it possessed multiple same carbon and proton resonances (Table 2). A close inspection of the NMR spectra revealed that C-14 was substituted with a hydroxyl group, which was supported by $^1$H-$^1$H COSY correlation OH-14/H-14 and HMBC correlation of OH-14 with C-14. The two methoxyl groups were decided to be placed at C-3 and C-7 via the HMBC correlations of OCH$_3$-3 with C-3, OCH$_3$-7 with C-7, and the NOESY correlations OCH$_3$-3/H-4 and OCH$_3$-7/H-8. Relative configuration of compound (5) was assigned on the basis of NOE correlation and coupling constant. The small coupling constant (J=1.8 Hz) between H-13a and H-14 and strong NOE correlation H-13a/H-14 led to the cis configuration of both protons (Damu, A. G. et al., Planta Med., 2009, 75, 1152-1156, Stærk, D. et al., J. Nat. Prod., 2000, 63, 1584-1586). The absolute stereochemistry of compound (5) was inferred from its optical rotation and CD spectrum. The positive optical rotation and the negative Cotton effect at 261 nm in the CD spectrum indicated the S configuration at C-13a (Damu, A. G. et al., Planta Med., 2009, 75, 1152-1156, Stærk, D. et al., J. Nat. Prod., 2000, 63, 1584-1586, S. F, J. F. Mi, et al., Acta Pharm. Sin. B, 27, 197-203). Overall, the data above contributed to the characterization of compound (5) as 2-hydroxyl tylophorinidine (i.e. having Formula (III) above, wherein R$_1$ is OH, R$_2$ is OCH$_3$, R$_3$ is OH and R$_4$ is α-OH).

2-hydroxyl tylophorinidine (compound (5)). White powder; $[\alpha]_D^{24}$ +13 (c 0.18 CHCl$_3$-MeOH 4:1); UV (MeOH) $\lambda_{max}$ (log ∈) 250 (4.60, sh), 258 (4.73), 290 (4.49), 304 (4.26, sh) nm; CD (MeOH) 261 (Δ□ −0.26) nm; $^1$H and $^{13}$C NMR data, see Tables 1 and 2; HRESIMS m/z 382.1665 [M+H]$^+$ (calcd for C$_{22}$H$_{23}$NO$_5$, 382.1649).

Compound (6) was obtained as brown amorphous solid. Its molecular formula was determined as C$_{21}$H$_{21}$NO$_5$ by peak at m/z 368.1500 ([M+H]$^+$, calcd 368.1492). The NMR data of compound (6) closely resembled those of compound (13) with differences ascribed to the resonances at 9, 11, 13a, and 14 (Huang, X. et al., Planta Med., 2004, 70, 441-445, Damu, A. G. et al., J. Nat. Prod., 2005, 68, 1071-1075) (Tables 1 and 2). In the $^1$H-NMR spectrum of 6 (Table 1), downfield shifts of H-9 ($\delta_H$ 5.13, 4.78), H-11 ($\delta_H$ 3.63, 3.57), H-13a ($\delta_H$ 3.64), H-14 ($\delta_H$ 5.10) (Table 1) were observed with reference to those of compound (13) (see Tables 4 to 6). Likewise, deshielding carbon resonances at C-9 ($\delta_c$ 65.9), C-11 ($\delta_c$ 69.3), C-13a ($\delta_c$ 69.4) (Table 2) were observed in $^{13}$C-NMR spectrum. The aforementioned data indicated that compound (6) was definitely a N-oxide analogue of compound (13). The methoxyl group was thus connected to C-7 on the basis of HMBC correlation of OCH$_3$-7 with C-7, and NOESY correlation OCH$_3$-7/H-8. Neither coupling constant nor NOE was observed between H-13a and H-14. Therefore, H-14 was assigned to be trans to H-13a. The appearance of H-13a signal at $\delta_H$ 3.64 (Table 1) indicated no substituent effects of axial N-oxides, prompting the trans configuration of N-oxide to H-13a (Damu, A. G. et al., J. Nat. Prod., 2005, 68, 1071-1075, Lavault, M. et al., Pharm. Acta Helv., 1994, 68, 225-227). Compound (6) displayed a positive optical rotation and a negative Cotton effect at 242 nm in the CD spectrum, indicating S configuration at C-13a (Damu, A. G. et al., Planta Med., 2009, 75, 1152-1156, Stærk, D. et al., J. Nat. Prod., 2000, 63, 1584-1586, S. F, J. F. Mi et al., Acta Pharm. Sin. B, 27, 197-203). As a result, compound (6) was established as 10R, 14R-3-O-demethyl tylophorinidine N-oxide (i.e. having Formula (IV), wherein $R_1$ is H, $R_2$ is OH, $R_3$ is OH and $R_4$ is β-OH).

10R, 14R-3-O-demethyl tylophorinidine N-oxide (compound (6)). Brown amorphous solid; $[\alpha]_D^{30}$ +16 (c 0.32 DMSO-MeOH 1:1); UV (MeOH) $\lambda_{max}$ (log ∈) 250 (4.43, sh), 258 (4.51), 285 (4.23), 315 (3.79) nm; CD (MeOH) 242 (Δε-5.37) nm; $^1$H and $^{13}$C NMR data, see Tables 1 and 2; HRESIMS m/z 368.1500 [M+H]$^+$ (calcd for $C_{21}H_{21}NO_5$, 368.1492).

HRESIMS analysis of compound (7) gave a protonated molecule at m/z 398.1604 [M+H]$^+$, which was consistent with the molecular formula $C_{22}H_{23}NO_6$ (calcd 398.1590). Compound (7) was the N-oxide analogue of compound (5) on the basis of the deshielding signals at 9, 11, 13a, and 14 (Huang, X. et al., Planta Med., 2004, 70, 441-445, Damu, A. G. et al., J. Nat. Prod., 2005, 68, 1071-1075) (Tables 1 and 2). In the $^1$H-NMR spectrum of compound (7), downfield shifts of H-9 ($\delta_H$ 5.20, 4.86), H-11 ($\delta_H$ 3.71, 3.63), H-13a ($\delta_H$ 3.73), H-14 ($\delta_H$ 5.03) were observed with reference to those of 5 (Table 1). Likewise, deshielding carbon resonances at C-9 ($\delta_c$ 66.0), C-11 ($\delta_c$ 69.3), C-13a ($\delta_c$ 69.4) were observed in $^{13}$C-NMR spectrum (Table 2). The methoxyl groups were thus connected to C-3 and C-7 on the basis of HMBC correlation of $OCH_3$-3 with C-3, $OCH_3$-7 with C-7, and NOESY correlations $OCH_3$-3/H-4, $OCH_3$-7/H-8. The hydroxyl groups were determined to be placed at C-2 and C-6 based on the carbon signals at $\delta_c$ 146.7 and 147.2 (Table 2). The small coupling constant (J=1.8 Hz) between H-13a and H-14 and strong NOE correlation H-13a/H-14 revealed cis orientation of both protons (Damu, A. G. et al., Planta Med., 2009, 75, 1152-1156, Stærk, D. et al., J. Nat. Prod., 2000, 63, 1584-1586). The appearance of H-13a signal at $\delta_H$ 3.73 (Table 1) indicated no substituent effects of axial N-oxides. Hence, the configuration of N-oxide was determined to be trans to H-13a (Damu, A. G. et al., J. Nat. Prod., 2005, 68, 1071-1075, Lavault, M. et al., Pharm. Acta Helv., 1994, 68, 225-227). Absolute configuration of compound (7) was assigned via comparing its optical rotation value with known compound. Since compound (5) had a specific optical activity of $[\alpha]_D^{24}$ +13 (c 0.18 CHCl$_3$-MeOH 4:1), the negative optical rotation of compound (7) suggested the R configuration at C-13a (Lee, Y. Z. et al., Planta Med., 2011, 77, 1932-1938, Lykkeberg, A. K. et al., J. Nat. Prod., 2002, 65, 1299-1302) tentatively. Therefore, compound (7) was established as 10S, 13aR, 14R-2-hydroxyl tylophorinidine (i.e. having Formula (V)).

10S, 13aR, 14R-2-hydroxyl tylophorinidine N-oxide (compound (7)). White powder; $[\alpha]_D^{26}$ –307 (c 0.02 DMSO-MeOH 3:5); UV (MeOH) $\lambda_{max}$ (log ∈) 258 (4.54), 282 (4.18, sh), 288 (4.23), 304 (3.97, sh) nm; $^1$H and $^{13}$C NMR data, see Tables 1 and 2; HRESIMS m/z 398.1604 [M+H]$^+$ (calcd for $C_{22}H_{24}NO_6$, 398.1590).

The molecular formula of compound (8) was assigned as $C_{23}H_{25}NO_6$ by HRESIMS ([M+H]$^+$, m/z 412.1766; calcd 412.1755), which showed one methylene more than that of compound (7). The NMR data of compound (8) closely matched those of compound (7) (Tables 1 and 2) except for the presence of an additional methoxyl group instead of hydroxyl group at C-6, which was further confirmed by HMBC correlation of $OCH_3$-6 with C-6 together with NOESY correlation $OCH_3$-6/H-5. The remaining two methoxyl groups were placed at C-3 and C-7 based on HMBC correlations of $OCH_3$-3 with C-3, $OCH_3$-7 with C-7, as well as the NOESY correlations $OCH_3$-3/H-4 and $OCH_3$-7/H-8. The hydroxyl group was connected to C-2 based on the carbon resonance at $\delta_c$ 147.0 (Table 2). H-14 was assigned to be trans to H-13 since no coupling constant nor NOE was observed between both. The configuration of N-oxide was determined to be trans to H-13a due to the appearance of H-13a signal at $\delta_H$ 3.76 (Table 1) without substituent effects of axial N-oxides (Damu, A. G. et al., J. Nat. Prod., 2005, 68, 1071-1075, Lavault, M. et al., Pharm. Acta Helv., 1994, 68, 225-227). The positive optical rotation value and the negative Cotton effect at 259 nm in the CD spectrum indicated the S configuration at C-13a (Damu, A. G. et al., Planta Med., 2009, 75, 1152-1156, Stærk, D. et al., J. Nat. Prod., 2000, 63, 1584-1586, S. F, J. F. Mi et al., Acta Pharm. Sin. B, 27, 197-203). Therefore, compound (8) was determined as 10R-2-hydroxyl tylophorinine N-oxide (i.e. having Formula (IV) above, wherein $R_1$ is OH, $R_2$ is $OCH_3$, $R_3$ is $OCH_3$ and $R_4$ is β-OH).

10R-2-hydroxyl tylophorinine N-oxide (compound (8)). White powder; $[\alpha]_D^{24}$ +94 (c 0.19 CHCl$_3$-MeOH 1:1); UV (MeOH) $\lambda_{max}$ (log ∈) 260 (4.22), 289 (3.97), 305 (3.72, sh) nm; CD (MeOH) 227 (Δε –0.88), 259 (40-2.56) nm; $^1$H and $^{13}$C NMR data, see Tables 1 and 2. HRESIMS m/z 412.1766 [M+H]$^+$ (calcd for $C_{23}H_{25}NO_6$, 412.1755).

Compound (9) was obtained as white powder. The molecular formula $C_{23}H_{25}NO_5$ was deduced from HRESIMS peak at m/z 396.1803 ([M+H]$^+$, calcd 396.1805 for $C_{23}H_{26}NO_5$). Compound (9) possessed similar NMR data as those of compound (21) (Tables 1 and 2) (Zhen, Y. et al., Acta Bot. Sin., 2002, 44, 349-353). The difference was attributed to the additional hydroxyl group placed at C-2 on the basis of the carbon signals at $\delta_c$ 146.7 (Table 2). The HMBC correlations of $OCH_3$-3 with C-3, $OCH_3$-6 with C-6, $OCH_3$-7 with C-7, and NOESY correlations $OCH_3$-3/H-4, $OCH_3$-6/H-5, $OCH_3$-7/H-8 collectively indicated the placement of the methoxyl groups at C-3, C-6, C-7. The strong NOE correlation H-13a/H-14 indicated the cis configuration of both protons (Lee, Y. Z. et al., Planta Med., 2011, 77, 1932-1938).

The negative optical rotation value and the positive Cotton effect at 239 nm in the CD spectrum indicated the R stereochemistry at C-13a (Damu, A. G. et al., Planta Med., 2009, 75, 1152-1156, Stærk, D. et al., J. Nat. Prod., 2000, 63, 1584-1586, S. F, J. F. Mi et al., Acta Pharm. Sin. B, 27, 197-203). Thus compound (9) was elucidated as 13aR-2-hydroxyl tylophorinine (i.e. having Formula (VI)). Compound (9) was isolated as chloric salt form for it was treated with hydrochloric acid before subjected to chromatography for purification.

13aR-2-hydroxyl tylophorinine (compound (9)). White powder; $[\alpha]_D^{23}$ –23 (c 0.3 CHCl$_3$); UV (CHCl$_3$) $\lambda_{max}$ (log ∈) 249 (4.37, sh), 259 (4.53), 290 (4.30), 303 (4.08) nm; CD (MeOH) 239 (Δε+5.90) nm; $^1$H and $^{13}$C NMR data, see Tables 1 and 2; HRESIMS m/z 396.1803 [M+H]$^+$ (calcd for $C_{23}H_{25}NO_5$, 396.1805).

Compound (10) was obtained as white powder. The molecular formula $C_{24}H_{27}NO_6$ was deduced from HRESIMS peak at m/z 426.1901 ([M+H]$^+$, calcd 426.1911). The NMR data of compound (10) (Tables 1 and 2) corresponding to the phenanthrene moiety closely resembled those of 14β-hydroxytylophorine N-oxide, suggesting it to be an isomer (Nakano, D. et al., J. Nat. Med., 2015, 69, 397-401). The methoxyl groups inferred from $^1$H NMR spectrum were thus placed at C-2, C-3, C-6, C-7 based on HMBC correlations of $OCH_3$-2 with C-2, $OCH_3$-3 with C-3, $OCH_3$-6 with C-6, $OCH_3$-7 with C-7, as well as the NOESY correlations $OCH_3$-2/H-1, $OCH_3$-3/H-4, $OCH_3$-6/H-5, $OCH_3$-7/H-8. The small coupling constant (J=2.4 Hz) between H-13a and H-14 and the strong NOE correlation H-13a/H-14 led to the configuration of H-14, which was cis to H-13a (Damu, A. G. et al., Planta Med., 2009, 75, 1152-1156, Stærk, D. et al., J. Nat. Prod., 2000, 63, 1584-1586). The appearance of H-13a signal at $\delta_H$ 3.73 (Table 1) indicated no substituent effects of axial N-oxides. Hence, the configuration of N-oxide was determined to be trans to H-13a (Damu, A. G. et al., J. Nat. Prod., 2005, 68, 1071-1075, Lavault, M. et al., Pharm. Acta Helv., 1994, 68, 225-227). The positive optical rotation value and the negative Cotton effect at 279 nm in the CD spectrum suggest S configuration at C-13a (Damu, A. G. et al., Planta Med., 2009, 75, 1152-1156, Stærk, D. et al., J. Nat. Prod., 2000, 63, 1584-1586, S. F, J. F. Mi et al., Acta Pharm. Sin. B, 27, 197-203). Thus, compound (10) was identified as 10R, 13aS, 14S-14-hydroxytylophorine N-oxide (i.e. having Formula (IV) above, wherein $R_1$ is $OCH_3$, $R_2$ is $OCH_3$, $R_3$ is $OCH_3$ and $R_4$ is $\alpha$-OH).

10R, 13aS, 14S-14-hydroxytylophorine N-oxide (compound (10)). White powder; $[\alpha]_D^{23}$ +25 (c 0.29 $CHCl_3$); UV ($CHCl_3$) $\lambda_{max}$ (log $\in$) 260 (4.73), 288 (4.48), 305 (4.19, sh), 313 (3.81, sh) nm; CD (MeOH) 279 ($\Delta\epsilon$ -1.92) nm; IR (KBr): $v_{max}$=3397, 2965, 1620, 1514, 1473, 1427, 1255, 1213, 1197, 1151, 1035, 1012, 846, 781 $cm^{-1}$; $^1H$ and $^{13}C$ NMR data, see Tables 1 and 2; HRESIMS m/z 426.1901 $[M+H]^+$ (calcd for $C_{24}H_{27}NO_6$, 426.1911).

Compound (11) was obtained as white powder. The molecular formula $C_{24}H_{27}NO_5$ was deduced from HRESIMS peak at m/z 410.1956 ($[M+H]^+$, calcd 410.1962). The NMR data of compound (11) (Tables 1 and 2) corresponding to the phenanthrene moiety closely matched those of 10R, 13aR tylophorine N-oxide, suggesting it to be an isomer (Damu, A. G. et al., J. Nat. Prod., 2005, 68, 1071-1075). Consequently, the four methoxyl groups deducing from $^1H$ NMR spectral data were placed at C-2, C-3, C-6, and C-7. This was further confirmed by the observed HMBC correlations of $OCH_3$-2 with C-2, $OCH_3$-3 with C-3, $OCH_3$-6 with C-6, $OCH_3$-7 with C-7, and NOESY correlations $OCH_3$-2/H-1, $OCH_3$-3/H-4, $OCH_3$-6/H-5, $OCH_3$-7/H-8. The appearance of H-13a signal at $\delta_H$ 3.76 (Table 1) indicated no substituent effects of axial N-oxides. Hence, the configuration of N-oxide was determined to be trans to H-13a (Damu, A. G. et al., J. Nat. Prod., 2005, 68, 1071-1075, Lavault, M. et al., Pharm. Acta Helv., 1994, 68, 225-227). Compound (11) displayed a positive optical rotation value and a negative Cotton effect at 238 nm in the CD spectrum, suggesting S configuration at C-13a (Damu, A. G. et al., Planta Med., 2009, 75, 1152-1156, Stærk, D. et al., J. Nat. Prod., 2000, 63, 1584-1586, S. F, J. F. Mi et al., Acta Pharm. Sin. B, 27, 197-203). Thus, compound (11) was identified as 10R, 13aS-tylophorine N-oxide (i.e. having Formula (IV) above, wherein $R_1$ is $OCH_3$, $R_2$ is $OCH_3$, $R_3$ is $OCH_3$ and $R_4$ is H).

10R, 13aS-tylophorine N-oxide (compound (11)). White powder; $[\alpha]_D^{24}$ +78 (c 0.67 $CHCl_3$-MeOH 3:1); UV ($CHCl_3$) $\lambda_{max}$ (log $\in$) 258 (4.90), 289 (4.66), 304 (4.42) nm; CD (MeOH) 238 ($\Delta\epsilon$ -2.04) nm; $^1H$ and $^{13}C$ NMR data, see Tables 1 and 2; HRESIMS m/z 410.1956 $[M+H]^+$ (calcd for $C_{24}H_{27}NO_5$, 410.1962).

Compound (12) was obtained as white powder. Compound (12) was assigned a molecular formula $C_{23}H_{25}NO_4$ from its HRESIMS peak at m/z 380.1849 ($[M+H]^+$, calcd 380.1856), one oxygen atom more than that of 20 (Lv, H. et al, PLoS One, 2012, 7, e30342). Compound (12) possessed similar NMR data as those of compound (20) (Tables 1 and 2). The distinctive signals were attributed to the downfield shifts observed at H-9 ($\delta_H$ 5.67, 4.69), H-11 ($\delta_H$ 4.45, 3.68), H-13a ($\delta_H$ 3.45) in the $^1H$ NMR spectrum and C-9 ($\delta_c$ 64.4), C-11 ($\delta_c$ 68.3), C-13a ($\delta_c$ 70.5) in the $^{13}C$ NMR spectrum with respect to those of 20 (Lv, H. et al., PLoS One, 2012, 7, e30342) (Table 2). The aforementioned information suggested the presence of N-oxide functionality. The three methoxyl groups deduced from $^1H$ NMR spectrum were determined to be placed at C-3, C-6, and C-7 by HMBC correlations of $OCH_3$-3 with C-3, $OCH_3$-6 with C-6, $OCH_3$-7 with C-7, and NOESY correlations $OCH_3$-3/H-4, $OCH_3$-6/H-5, $OCH_3$-7/H-8. The appearance of H-13a signal at $\delta_H$ 3.76 (Table 1) indicated no substituent effects of axial N-oxides. Hence, the configuration of N-oxide was determined to be trans to H-13a (Damu, A. G. et al., J. Nat. Prod., 2005, 68, 1071-1075, Lavault, M. et al., Pharm. Acta Helv., 1994, 68, 225-227). The positive optical rotation value and the negative Cotton effect at 234 nM in the CD spectrum suggest S configuration at C-13a (Damu, A. G. et al., Planta Med., 2009, 75, 1152-1156, Stærk, D. et al., J. Nat. Prod., 2000, 63, 1584-1586, S. F, J. F. Mi et al., Acta Pharm. Sin. B, 27, 197-203). Thus, compound (12) was identified as 10R-deoxytylophorinine N-oxide (i.e. having Formula (IV) above, wherein $R_1$ is H, $R_2$ is $OCH_3$, $R_3$ is $OCH_3$ and $R_4$ is H).

10R-deoxytylophorinine N-oxide (compound (12)). White powder; $[\alpha]_D^{24}$ +54 (c 0.46 $CHCl_3$); UV ($CHCl_3$) $\lambda_{max}$ (log $\in$) 260 (4.39), 286 (4.27), 313 (3.60) nm; CD (MeOH) 234 ($\Delta\epsilon$ -4.15) nm; $^1H$ and $^{13}C$ NMR data, see Tables 1 and 2; HRESIMS m/z $[M+H]^+$ (calcd for $C_{23}H_{25}NO_4$).

The known compounds were characterized as 11-keto-O-methyl tylophorinidine (compound (2)) (Lv, H. et al., PLoS One, 2012, 7, e30342), 3-O-demethyl tylophorinidine (compound (13)) (Dhiman, M. et al., Chem. Pap.-Chem. Zvesti, 2013, 67, 245-248), tylophorinidine (compound (14)) (Zhen, Y. et al., Acta Bot. Sin., 2002, 44, 349-353), trans-(+)-3,14a-dihydroxy-6,7-dimethoxyphenanthroindolizidine (compound (15)) (Komatsu, H. et al., J. Med. Chem., 2001, 44, 1833-1836), tylophoridicine C (compound (16)) (Huang, X. et al., Planta Med., 2004, 70, 441-445), tylophorinine N-oxide (compound (17)) (Abe, F. et al., Phytochemistry, 1995, 39, 695-699), tylophorinine (compound (18)) (Y Zhen, Y. et al., Acta Bot. Sin., 2002, 44, 349-353), 13aS-tylophorine (compound (19)) (Lee, Y. Z. et al., Planta Med., 2011, 77, 1932-1938), deoxytylophorinine (compound (20)) (Wang, Z. et al., PloS one, 2012, 7, e52933), O-methyl-tylophorindine (compound (21)) (Y Zhen, Y. et al., Acta Bot. Sin., 2002, 44, 349-353), tylophoridicine D (compound (22)) (Huang, X. et al., Planta Med., 2004, 70, 441-445) by comparing their NMR and optical rotation data with those reported in the literature (see Tables 4 to 6).

TABLE 1

$^1$H-NMR (600 MHz) data for compounds (1) and (4) to (12) ($\delta$ in ppm, J in Hz).

| NO. | 1+ | 4+ | 5+ | 6+ | 7+ | 8+ | 9+ | 10+ | 11+ | 12+ |
|---|---|---|---|---|---|---|---|---|---|---|
| 1 | 8.14, d, 9 | 7.25, s | 7.61, s | 7.95, d, 9 | 7.52, s | 7.55, s | 7.66, s | 7.56, s | 7.31, s | 7.85$^e$, d 9.6 |
| 2 | 7.25, dd, 2.4, 9 | | | 7.05, dd, 2.4, 9 | | | | | | 7.23, dd, 2.4, 9 |
| 4 | 7.89, d, 2.4 | 7.82, s | 7.79, s | 7.70, d, 2.4 | 7.82, s | 8.02, s | 7.98, s | 8.04$^b$, s | 7.80$^c$ | 7.84$^e$ |
| 5 | 8.10, s | 7.95, s | 7.95, s | 7.85, s | 8.00, s | 8.04, s | 8.00, s | 8.06$^b$, s | 7.79$^c$ | 7.82, s |

TABLE 1-continued

¹H-NMR (600 MHz) data for compounds (1) and (4) to (12) (δ in ppm, J in Hz).

| NO. | 1+ | 4+ | 5+ | 6+ | 7+ | 8+ | 9+ | 10+ | 11+ | 12+ |
|---|---|---|---|---|---|---|---|---|---|---|
| 8 | 7.28, s | 7.14, s | 7.17, s | 7.11, s | 7.16, s | 7.18, s | 7.19, s | 7.19, s | 6.95, s | 6.85, s |
| 9 | 5.17, d, 17.4 | 4.52, d, 15 | 4.55, d, 15.6 | 5.13, d, 15 | 5.20, d, 15.6 | 5.22, d, 15 | 4.57, d, 15 | 5.23, d, 15 | 5.30, d, 14.4 | 5.67, d, 11.4 |
|  | 4.51, d, 17.4 | 3.47, d, 15 | 3.43, d, 15.6 | 4.78, d, 15 | 4.86, d, 15.6 | 4.90, d, 15 | 3.48, d, 15 | 4.87, d, 15 | 4.71, d, 13.8 | 4.69, d, 15 |
| 11 |  | 3.30, m | 3.30, m | 3.63, m | 3.73, m | 3.71, m | 3.32, m | 3.71, m | 4.14, m | 4.45, m |
|  |  | 2.31, m | 2.38, m | 3.57, m | 2.61, m | 3.63, m | 2.38, m | 3.63, m | 3.61, m | 3.68, m |
| 12 | 2.44, m | 1.82, m | 1.82, m | 2.27, m | 2.33, m | 2.33, m | 1.83, m | 2.34, m | 2.63, m | 2.52, m |
|  | 2.37, m | 1.83, m | 1.82, m | 2.02, m | 2.14, m | 2.07, m | 1.83, m | 2.09, m | 2.09, m | 2.15, m |
| 13 | 2.36, m | 2.13, m | 2.17, m | 2.64, m | 2.70, m | 2.71, m | 2.20, m | 2.72, m | 2.44, m | 2.30, m |
|  | 2.19, m | 1.60, m | 1.83, m | 2.05, m | 2.14, m | 2.14, m | 1.84, m | 2.12, m | 2.27, m | 2.30, m |
| 13a | 3.91, m | 2.34, m | 2.39, m | 3.64, m | 3.73, m | 3.76, m | 2.42, m | 3.73, m | 3.48, m | 3.45, m |
| 14 | 5.09, dd, 2.4, 7.2 | 3.17, m | 4.76, dd, 1.8, 9.6 | 5.10, brs | 5.03, d, 1.8 | 5.06, brs | 4.80, br | 5.19, d, 2.4 | 3.56, m | 3.41, m |
|  |  | 2.65, m |  |  |  |  |  |  | 3.24, m | 3.30, m |
| OCH₃-2 |  |  |  |  |  |  |  |  | 3.92, s | 4.07, s |
| OCH₃-3 | 3.98, s | 3.99, s | 3.98, s |  | 4.00, s | 4.06ᵃ, s | 4.04, s | 4.06, s | 4.15ᵈ, s | 4.06, s |
| OCH₃-6 |  |  |  |  |  | 4.05ᵃ, s | 4.03, s | 4.05, s | 4.13ᵈ, s | 4.11, s |
| OCH₃-7 | 4.02, s | 3.93, s | 3.93, s | 3.92, s | 3.96, s | 3.95, s | 3.92, s | 3.96, s | 4.02, s | 3.94, s |
| OH-14 | 5.41, d, 7.2 |  | 4.46, d, 9.6 |  |  |  |  |  |  |  |

+Measured in DMSO-d₆.
*Measured in CDCl₃.
ᵃ⁻ᵉOverlapped signals.

TABLE 2

¹³C-NMR (150 MHz) data for compounds (1) and (4) to (12) (δ in ppm).

| NO. | 1+ | 4+ | 5+ | 6+ | 7+ | 8+ | 9+ | 10+ | 11* | 12* |
|---|---|---|---|---|---|---|---|---|---|---|
| 1 | 125.9 | 107.6 | 109.2 | 127.0 | 109.5 | 109.5 | 109.7 | 105.8 | 104.0 | 125.1 |
| 2 | 115.9 | 146.2 | 146.1 | 116.9 | 146.7 | 147.0 | 146.7 | 149.0 | 149.0ᵈ | 115.3 |
| 3 | 157.4 | 147.7 | 147.7 | 156.2 | 148.6 | 148.8 | 148.3 | 149.4 | 148.9ᵈ | 158.1 |
| 4 | 103.5 | 103.7 | 103.4 | 106.1 | 103.8 | 104.5ᵇ | 104.2 | 104.3ᶜ | 103.4ᵉ | 104.5 |
| 5 | 108.0 | 107.4 | 107.4 | 108.0 | 107.9 | 104.5ᵇ | 104.4 | 104.6ᶜ | 103.2ᵉ | 103.9 |
| 6 | 146.9 | 146.0 | 146.6 | 147.4 | 147.2 | 149.4 | 149.2 | 149.2 | 148.8ᵈ | 148.7 |
| 7 | 148.9 | 147.6 | 147.6 | 149.3 | 148.2 | 148.9 | 148.0 | 149.1 | 148.7ᵈ | 149.7 |
| 8 | 103.8 | 103.4 | 103.9 | 104.6 | 104.5 | 104.4 | 104.5 | 104.3 | 102.6 | 102.5 |
| 9 | 40.3 | 53.5 | 53.8 | 65.9 | 66.0 | 66.0 | 54.1 | 66.0 | 66.4 | 64.4 |
| 11 | 173.5 | 54.6 | 55.0 | 69.3 | 69.3 | 69.4 | 55.3 | 69.4 | 69.9 | 68.3 |
| 12 | 30.3 | 21.3 | 21.7 | 20.3 | 20.4 | 20.4 | 22.1 | 20.4 | 20.1 | 19.8 |
| 13 | 19.2 | 30.9 | 24.0 | 22.3 | 22.3 | 22.3 | 24.4 | 22.4 | 27.3 | 27.1 |
| 13a | 57.7 | 60.0 | 65.1 | 69.4 | 69.4 | 69.3 | 65.4 | 69.3 | 69.7 | 70.5 |
| 14 | 63.5 | 33.2 | 64.0 | 64.0 | 64.2 | 64.2 | 64.4 | 64.1 | 27.6 | 27.2 |
| 4a | 130.2 | 125.4 | 122.7 | 130.9 | 123.3 | 123.6 | 126.4 | 124.3 | 123.7 | 130.8 |
| 4b | 124.2 | 123.7 | 124.5 | 124.5 | 125.2ᵃ | 124.8 | 123.4 | 123.2 | 123.9 | 123.7 |
| 8a | 123.1 | 122.6 | 122.1 | 123.4 | 122.1 | 122.8 | 124.5 | 124.5 | 124.9ᶠ | 124.4 |
| 8b | 123.5 | 125.9 | 126.7 | 119.4 | 120.7 | 120.6 | 123.2 | 120.8 | 120.4 | 118.6 |
| 14a | 127.5 | 124.6 | 128.0 | 128.7 | 127.9 | 128.6 | 127.0 | 128.9 | 124.7 | 124.5 |
| 14b | 124.1 | 122.2 | 125.8 | 123.5 | 125.3ᵃ | 125.5 | 129.2 | 125.0 | 124.0ᶠ | 124.0 |
| OCH₃-2 |  |  |  |  |  |  |  | 55.8 | 56.0ᵍ |  |
| OCH₃-3 | 55.3 | 55.6 | 55.6 |  | 55.9 | 56.4ᵈ | 56.4 | 56.3 | 55.9ᵍ | 55.5 |
| OCH₃-6 |  |  |  |  |  | 56.3ᵈ | 56.2 | 56.3 | 55.9ᵍ | 55.9 |
| OCH₃-7 | 55.7 | 55.5 | 55.6 | 56.1 | 56.1 | 56.0 | 55.9 | 56.1 | 55.9ᵍ | 56.0 |

+Measured in DMSO-d₆.
*Measured in CDCl₃.
ᵃ⁻ʲoverlapped signals

TABLE 3

¹H-NMR (600 MHz) and ¹³C-NMR (150 MHz) data for compound (3) (δ in ppm, J in Hz)ᵃ.

| position | δ$_H$ | δ$_C$ |
|---|---|---|
| 1 | 8.16, d, 9 | 127.2 |
| 2 | 7.24, dd, 2.4, 9 | 116.0 |
| 3 |  | 157.9 |
| 4 | 8.07, d, 2.4 | 104.8 |
| 5 | 8.10, s | 105.0 |
| 6 |  | 149.3 |
| 7 |  | 149.8 |
| 8 | 7.19, s | 104.4 |
| 9 | 4.76, d, 15; 3.85, d, 15 | 56.0 |
| 12 | 4.24, m | 74.1 |
| 13 | 1.81, m; 1.43, m | 30.5 |
| 14 | 2.33, m; 1.82, m | 24.9 |

TABLE 3-continued $^1$H-NMR (600 MHz) and $^{13}$C-NMR (150 MHz) data for compound (3) (δ in ppm, J in Hz)$^a$.

| position | $\delta_H$ | $\delta_C$ |
|---|---|---|
| 14a | 2.70, m | 64.9 |
| 15 | 4.93, d, 6 | 67.3 |
| 16 | 2.63, m; 2.63, m | 48.8 |
| 17 |  | 206.7 |
| 18 | 2.19, s | 30.7 |
| 4a |  | 130.8 |
| 4b |  | 124.4 |
| 8a |  | 124.2 |
| 8b |  | 123.8 |
| 15a |  | 128.6 |
| 15b |  | 124.3 |
| OCH$_3$-3 | 4.00, s | 55.9 |
| OCH$_3$-6 | 4.04, s | 56.3 |
| OCH$_3$-7 | 3.96, s | 55.9 |
| OH-15 | 5.11, d, 9.6 |  |

$^a$Measured in DMSO-d$_6$.

TABLE 4

$^1$H-NMR (600 MHz) data for compounds (2), (13) to (16) (δ in ppm, J in Hz).

| NO. | 2$^+$ | 13$^+$ | 14$^+$ | 15$^+$ | 16* |
|---|---|---|---|---|---|
| 1 | 8.17, d, 9 | 8.10, d, 9 | 8.17, d, 9 | 8.15, d, 9 | 8.05, d, 9 |
| 2 | 7.28, dd, 2.4, 9 | 7.06, dd, 2, 9 | 7.18, dd, 9, 2.4 | 7.11, dd, 9, 2.4 | 7.17, dd, 9, 2 |
| 4 | 8.10, d, 3 | 7.69, d, 2 | 7.83, d, 2.4 | 7.94, d, 2.4 | 7.73, s |
| 5 | 8.13, s | 7.83, s | 8.02, s | 7.93, s | 7.97, s |
| 8 | 7.29, s | 7.19, s | 7.11, s | 7.21, s | 7.10, s |
| 9 | 5.18, d, 17.4 | 4.54, d, 15 | 4.48, d, 15.6 | 4.55, d, 15 | 5.21 |
|  | 4.53, d, 17.4 | 3.43, d, 15 | 3.38, d, 15.6 | 3.46 | 4.85, d, 15 |
| 11 |  | 3.33, m | 2.30, m | 3.32 | 3.71, m |
|  |  | 2.37, m | 3.25, m | 2.37, m | 3.63, m |
| 12 | 2.39, m | 1.83, m | 1.79-1.82, m | 1.84, m | 2.33, m |
|  | 2.36, m | 1.83, m | 1.79-1.82, m | 1.84, m | 2.11, m |
| 13 | 2.35, m | 2.17, m | 1.79-1.82, m | 2.19, m | 2.70, m |
|  | 2.21, m | 1.83, m | 2.16, m | 1.85, m | 2.11, m |
| 13a | 3.92, m | 2.37, m | 2.33, m | 2.41, m | 3.76, m |
| 14 | 5.11, dd, 7.2, 1.8 | 4.89, dd, 1.8, 9.6 | 4.88, s | 4.93, dd, 10.2, 1.8 | 5.18, d, 3 |
| OCH$_3$-2 |  |  |  |  |  |
| OCH$_3$-3 | 4.01, s |  | 3.94, s |  | 3.95, s |
| OCH$_3$-6 | 4.06, s |  |  | 4.00, s |  |
| OCH$_3$-7 | 4.00, s | 3.94, s | 3.92, s | 3.94, s | 3.94, s |
| OH-14 | 5.46, d, 7.2 | 4.50, d, 9.6 |  | 4.59, d, 10.2 |  |

$^+$Measured in DMSO-d$_6$.
*Measured in CDCl$_3$.
$^a$Overlapped signals

TABLE 5

$^1$H-NMR (600 MHz) data for compounds (17) to (21) (δ in ppm, J in Hz).

| NO. | 17$^+$ | 18* | 19* | 20* | 21* |
|---|---|---|---|---|---|
| 1 | 8.13, d, 9 | 8.43, d, 9 | 7.32, s | 7.95, d, 9 | 8.44, d, 9 |
| 2 | 7.28, dd, 9, 2.4 | 7.27, dd, 9, 2.4 |  | 7.24, dd, 2.4, 9 | 7.27 |
| 4 | 8.10, d, 3 | 7.78, d, 2.4 | 7.84, s | 8.08, d, 2.4$^a$ | 7.74, d, 1.8 |
| 5 | 8.12, s | 7.65, s | 7.83, s | 8.09, s$^a$ | 7.56, s |
| 8 | 7.20, s | 6.35, s | 7.21, s | 7.17, s | 6.14 |
| 9 | 5.21, d, 15 | 3.59, d, 15.6 | 4.63, d, 14.4 | 4.56, d, 15 | 3.33, d, 14.4 |
|  | 4.87, d, 15 | 3.14, d, 15.6 | 3.68, d, 14.4 | 3.54, d, 15 | 2.99, d, 14.4 |
| 11 | 3.70, m | 2.42, m | 3.48, t, 8.1 | 3.35, m; 2.36, m | 3.27, t, 8.4 |
|  | 3.62, m | 3.33, m | 2.48, m | 2.36, m | 2.18, q, 8.4 |
| 12 | 2.33, m | 2.03, m | 2.04, m | 1.82, m | 2.02, m |
|  | 2.08, m | 1.93, m | 1.94, m | 1.82, m | 1.89, m |
| 13 | 2.70, m | 1.93, m | 2.25, m | 2.17, m | 2.40, m |
|  | 2.11, m | 2.27, m | 1.78, m | 1.60, m | 1.86, m |
| 13a | 3.73, m | 2.43, m | 2.50, m | 2.40, m | 2.33, m |
| 14 | 5.18, d, 3 | 4.98 brd | 3.37, dd, 2.1, 15.6 | 3.37, m | 4.91 |
|  |  |  | 2.92, t, 10.8, 15 | 2.79, m |  |
| OCH$_3$-2 |  |  | 4.06, s |  |  |
| OCH$_3$-3 | 4.02, s | 4.07, s | 4.12, s | 3.98, s | 4.05, s |
| OCH$_3$-6 | 4.05, s | 4.13, s | 4.12, s | 4.02, s | 4.10, s |
| OCH$_3$-7 | 3.97, s | 3.88, s | 4.05, s | 3.94, s | 3.80, s |
| OH-14 |  |  |  |  |  |

TABLE 6

13C-NMR (150 MHz) data for compounds (2), (13) to (17), (19) to (21) (δ in ppm).

| position | 2+ | 13+ | 14+ | 15+ | 16+ | 17+ | 19* | 20* | 21* |
|---|---|---|---|---|---|---|---|---|---|
| 1 | 126.5 | 126.9 | 127.4 | 126.9 | 126.4 | 127.1 | 104.0 | 125.4 | 126.7 |
| 2 | 116.2 | 116.6 | 116.6 | 116.7 | 115.9 | 116.2 | 148.7 | 115.9 | 114.8 |
| 3 | 158.0 | 155.7 | 158.2 | 155.8 | 157.4 | 158.1 | 148.7 | 157.8 | 157.5 |
| 4 | 104.4 | 106.0 | 104.4 | 106.5 | 103.1 | 104.7 | 103.3 | 105.1 | 104.1 |
| 5 | 105.0 | 107.8 | 108.8 | 104.4 | 108.1 | 105.0 | 103.4 | 105.1 | 102.9 |
| 6 | 149.5 | 147.0 | 149.7 | 149.6 | 149.0 | 149.4 | 148.4 | 148.7 | 148.6 |
| 7 | 150.0 | 149.1 | 147.7 | 149.0 | 146.9 | 149.9 | 148.5 | 149.8 | 148.4 |
| 8 | 104.1 | 104.5 | 104.9 | 104.3 | 103.9 | 104.4 | 103.1 | 103.8 | 102.7 |
| 9 | 40.5 | 54.1 | 55.9 | 54.0 | 65.2 | 65.9 | 54.1 | 53.8 | 53.4 |
| 11 | 174.1 | 55.4 | 54.6 | 55.3 | 68.9 | 69.2 | 55.2 | 55.0 | 55.5 |
| 12 | 30.8 | 22.1 | 22.6 | 22.1 | 19.9 | 20.3 | 21.6 | 21.7 | 21.9 |
| 13 | 19.7 | 24.5 | 25.0 | 24.4 | 21.9 | 22.3 | 31.3 | 31.3 | 23.9 |
| 13a | 58.1 | 65.4 | 65.9 | 65.4 | 69.0 | 69.3 | 60.2 | 60.3 | 65.4 |
| 14 | 64.0 | 64.1 | 64.6 | 64.1 | 63.5 | 64.0 | 33.8 | 33.5 | 64.5 |
| OCH$_3$-2 | | | | | | | 55.9 | | |
| OCH$_3$-3 | 56.0$^a$ | | 56.5 | 55.9 | 55.6 | 55.9 | 56.0 | 55.9 | 55.5 |
| OCH$_3$-6 | 56.3$^a$ | | | 55.9 | | 56.3 | 56.0 | 56.3 | 55.7 |
| OCH$_3$-7 | 55.9 | 56.0 | 56.3 | | 55.1 | 56.9 | 55.9 | 55.9 | 55.5 |
| C ring | 131.0 | 130.7 | 124.6 | 131.0 | 119.8 | 131.0 | 124.4 | 125.5$^b$ | 123.7 |
| | 124.2 | 129.4 | 125.0 | 130.2 | 123.1 | 124.5 | 123.4 | 130.4 | 124.1 |
| | 124.3 | 125.9 | 125.9 | 125.8 | 123.8 | 124.4 | 126.1 | 123.2 | 125.4 |
| | 123.8 | 124.4 | 127.5 | 124.7 | 124.3 | 120.3 | 125.9 | 125.2$^b$ | 128.8 |
| | 128.8 | 124.2 | 129.7 | 124.4 | 128.1 | 129.5 | 123.6 | 125.9 | 130.6 |
| | 124.7 | 124.0 | 131.1 | 123.8 | 130.4 | 124.3 | 126.3 | 127 | 126.2 |

+Measured in DMSO-d$_6$.
*Measured in CDCl$_3$.
$^{a-b}$Overlapped signals

Example 2

Inhibition of HIF-1 Transcriptional Activity

HIF-1-mediated reporter gene assay in T47D cells was used to evaluate the HIF-1 activation inhibitory effects of compounds (1) and (3) to (22) on inhibiting HIF-1 activation induced by hypoxia. Digoxin, a well-known HIF-1 inhibitor, was used as a positive control (Zhang, H. et al., PNAS, 2008, 105, 19579-19586).

The HIF-1-mediated reporter gene assay in T47D cells was performed according to a previous protocol with minor modification (Parhira, S. et al., Sci. Rep., 2014, 4, 4748). T47D cells (American Type Culture Collection) were cultured in DMEM medium (Invitrogen), supplemented with 10% (v/v) fetal serum (FBS) (Invitrogen), 100 U/mL penicillin, and 100 μg/mL streptomycin (Invitrogen) in a humidified atmosphere (5% CO$_2$ and 95% air) at 37° C. Cells (5×10$^6$) were co-transfected with the HRE-luciferase (Addgene) and Renilla plasmids using Lipofectamine 2000 (Invitrogen) according to the manufacturer's protocol. The transfected cells were seeded in 96-well plates with a density of 5×10$^4$/well and cultured in DMEM with 10% FBS overnight. After addition of the test compounds with different concentrations, the cells were incubated for 1 h, and then exposed to hypoxic (2% O$_2$/5% CO$_2$/93% N$_2$) or normoxic (5% CO$_2$/95% air) conditions at 37° C. for 20 h. Then the cells were lysed, and luciferase assay was performed using a Dual-Luciferase® reporter assay (Promega) kit according to the instructions of the manufacturer. Luciferase activities of both HRE and Renilla were determined by a multimode reader (Infinite 200 PRO, Teacan). HIF-1 transcriptional activity was shown by the ratio of firefly/Renilla luciferase activity. IC$_{50}$ values were determined from the dose-response curves using Prism software. The data were repeated by three independent experiments.

Most phenanthroindolizidine alkaloids exhibited extremely potent inhibitory effects with IC$_{50}$ values in the low nanomolar range. The potency of compound (14) (IC$_{50}$: 4 nM) and compound (17) (IC$_{50}$: 3 nM) were even comparable to Manassantin B (IC$_{50}$: 3 nM), the most potent natural HIF-1 inhibitor identified so far.

As evident from Table 7, compounds (4), (5), (7), (13) to (18) and (21) exhibited potent HIF-1 inhibitory activity in low nanomole scale with IC$_{50}$ values ranged from 3 to 37 nM, which means 8~100 fold more potent than digoxin. Cytotoxicity, assessed by MTT assay, proved that all compounds exert no significant cytotoxicity against T47D cells at their effective concentrations for the inhibition of HIF-1 activation (see Table 8). All experiments were independently performed at least three times.

TABLE 7

HIF-1 activation inhibitory activity of phenanthroindolizidine alkaloids (1) and (3) to (22)

IC$_{50}$ (nM)

| compounds | T47D$^a$ |
|---|---|
| 1 | >10000 |
| 3 | 2664 ± 1808 |
| 4 | 19 ± 2 |
| 5 | 10 ± 3 |
| 6 | 50 ± 35 |
| 7 | 37 ± 8 |
| 8 | 170 ± 106 |
| 9 | 489 ± 108 |
| 10 | 441 ± 138 |
| 11 | 930 ± 330 |
| 12 | 254 ± 75 |
| 13 | 10 ± 6 |
| 14 | 4 ± 1 |
| 15 | 6 ± 3 |
| 16 | 25 ± 7 |
| 17 | 3 ± 1 |
| 18 | 19 ± 6 |
| 19 | 438 ± 151 |
| 20 | 115 ± 53 |
| 21 | 13 ± 6 |
| 22 | >10000 |
| Digoxin | 302 ± 21 |

$^a$human breast tumor.

Values are means±SD, where SD=standard deviation.

TABLE 8

Cytotoxicity of phenanthroindolizidine alkaloids (3) to (22) against T47D cells under normoxic and hypoxic conditions.
$IC_{50}$ (nM)

| compounds | Normoxic | Hypoxic |
|---|---|---|
| 3 | >10000 | >20000 |
| 4 | >500 | >500 |
| 5 | >250 | >250 |
| 6 | >200 | >200 |
| 7 | >1000 | >1000 |
| 8 | >1000 | >1000 |
| 9 | >2000 | >2000 |
| 10 | >2000 | >2000 |
| 11 | >2000 | >2000 |
| 12 | >1000 | >2000 |
| 13 | >250 | >250 |
| 14 | >10 | >100 |
| 15 | >250 | >250 |
| 16 | >100 | >100 |
| 17 | >100 | >100 |
| 18 | >500 | >500 |
| 19 | >1000 | >2000 |
| 20 | >600 | >15000 |
| 21 | >500 | >12500 |

It follows that non-planarity at indolizidine moiety enhanced the HIF-1 inhibitory activity. The inhibitory effect of compound (20) ($IC_{50}$ 115 nM) was at least 8 times more potent than its dehydrogenated product (22) ($IC_{50}$>10000 nM), which possessed extended conjugated system at indolizidine ring resulting in higher planarity.

Furthermore, substitution at indolizidine ring exerted crucial influence on HIF-1 inhibitory activity of the phenanthroindolizidine alkaloids. Firstly, replacement of the C-11 methylene group with a keto group decreased the HIF-1 inhibitory potency, which was exemplified by the observation that compound (14) ($IC_{50}$ 4 nM) exhibited a remarkable increase in HIF-1 inhibitory activity comparing with its 11-keto analogue compound (1) ($IC_{50}$>10000 nM). Secondly, oxidation of the indolizidine amine caused deleterious effect on HIF-1 inhibitory activity. The N-oxide analogue compounds (11), (12), (16) ($IC_{50}$ 930, 254, 25 nM, respectively) possessed 2~6 times in inhibitory effects lower than their free amine counterparts (19), (20), (14) ($IC_{50}$ 438, 115, 4 nM, respectively). Third, hydroxylation at C-14 strengthened the HIF-1 inhibitory activity. Compound (10), (18)/(21) ($IC_{50}$ 441, 19/13 nM) were 2~8 times more active than their deoxygenated counterparts (11), (20) ($IC_{50}$ 930, 115 nM, respectively).

Besides, substitution types and patterns on the phenanthrene unit also played significant roles in HIF-1 inhibitory activity. First, substitution of hydroxyl/methoxyl group at C-2 gave rise to decrease in HIF-1 inhibitory activity. At least 2-fold loss was observed between compound (14) ($IC_{50}$ 4 nM) and its 2-hydroxylated counterpart compound (5) ($IC_{50}$ 10 nM), while at least 3-fold decrease were present between compounds (12), (20) ($IC_{50}$ 254, 115 nM, respectively) and their 2-methoxylated counterparts 11, 19 ($IC_{50}$ 930, 438 nM, respectively). Second, methylation of hydroxyl group at C-3 favored higher inhibitory activity. At least 2-fold increase was observed between compounds (13) ($IC_{50}$10 nM) and its 3-methylated analogue compound (14) ($IC_{50}$4 nM).

HIF-1 does not only play a crucial role in response of mammalian cells to hypoxia and a driving force in cancer progression (G. Melillo, Mol. Cancer Res., 2006, 4, 601-605), but does also represent a negative prognostic factor in cancer treatment (G. L. Semenza, Nat. Rev. Cancer, 2003, 3, 721-73). Numerous efforts had thus been undertaken to discover small molecule HIF-1 inhibitors from natural products, and many natural product based HIF-1 inhibitors had been characterized and summarized previously (Nagle, D. G. and Zhou, Y. D., Curr. drug targets, 2006, 7, 355-369). Among which, lignoid manassantins ($IC_{50}$ 3~30 nM) (Hodges, T. W. et al., J. Nat. Prod., 2004, 67, 767-771) and phenanthroquinolizidines alkaloids ($IC_{50}$ 8.7~48.1 nM) (Cai, X. F. et al., J. Nat. Prod., 2006, 69, 1095-1097) were discovered to exhibit remarkable potency with Manassantin B ($IC_{50}$ 3 nM) considered as the most potent natural HIF-1 inhibitor so far (Hodges, T. W. et al., J. Nat. Prod., 2004, 67, 767-771). In the above experiment, compounds (14) ($IC_{50}$ 4 nM), (17) ($IC_{50}$ 3 nM) displayed comparable potency to Manassantin B. Collectively, the data above indicate that the isolated phenanthroindolizidine alkaloids are potent HIF-1 inhibitors.

The invention claimed is:

1. A method of treating a subject suffering from breast cancer comprising administering to the subject an effective amount of at least one phenanthroindolizidine alkaloid isolated from *Tylophora atrofolliculata*, wherein the phenanthroindolizidine alkaloid is selected from the group consisting of a phenanthroindolizidine alkaloid:

having Formula (III):

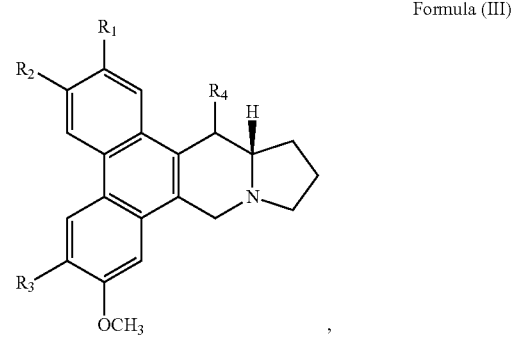

Formula (III)

wherein $R_1$ is OH, $R_2$ is $OCH_3$, $R_3$ is OH and $R_4$ is H;

having Formula (III) given above, wherein $R_1$ is OH, $R_2$ is $OCH_3$, $R_3$ is OH and $R_4$ is α-OH;

having Formula (III) given above, wherein $R_1$ is H, $R_2$ is OH, $R_3$ is OH and $R_4$ is α-OH;

having Formula (III) given above, wherein $R_1$ is H, $R_2$ is $OCH_3$, $R_3$ is OH and $R_4$ is α-OH;

having Formula (III) given above, wherein $R_1$ is H, $R_2$ is OH, $R_3$ is $OCH_3$ and $R_4$ is α-OH;

having Formula (III) given above, wherein $R_1$ is H, $R_2$ is $OCH_3$, $R_3$ is $OCH_3$ and $R_4$ is β-OH;

having Formula (III) given above, wherein $R_1$ is $OCH_3$, $R_2$ is $OCH_3$, $R_3$ is $OCH_3$ and $R_4$ is H;

having Formula (III) given above, wherein $R_1$ is H, $R_2$ is $OCH_3$, $R_3$ is $OCH_3$ and $R_4$ is H;

having Formula (III) given above, wherein $R_1$ is H, $R_2$ is $OCH_3$, $R_3$ is $OCH_3$ and $R_4$ is α-OH;

having Formula (IV):

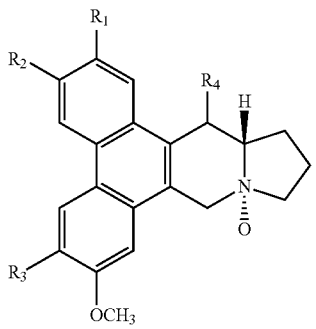

Formula (IV)

wherein R₁ is H, R₂ is OH, R₃ is OH and R₄ is β-OH;
having Formula (IV) given above, wherein R₁ is OH, R₂ is OCH₃, R₃ is OCH₃ and R₄ is β-OH;
having Formula (IV) given above, wherein R₁ is H, R₂ is OCH₃, R₃ is OCH₃ and R₄ is H;
having Formula (V):

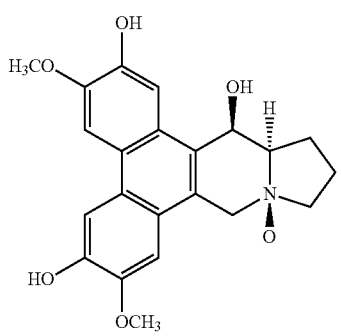

Formula (V)

having Formula (VII):

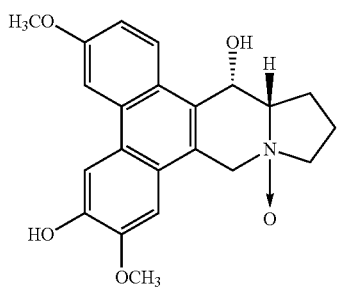

Formula (VII)

having Formula (VIII):

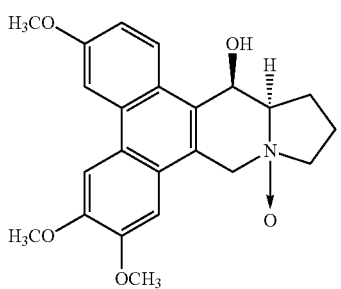

Formula (VIII)

2. A method of treating a subject suffering from breast cancer comprising administering an effective amount of a phenanthroindolizidine alkaloid selected from the group consisting of the following formulas to the subject:
Formula (III):

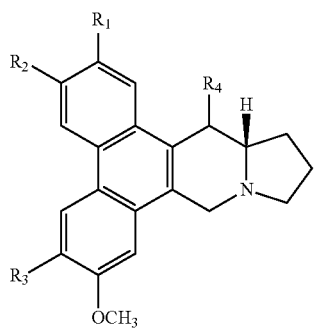

Formula (III)

wherein R₁ is OH, R₂ is OCH₃, R₃ is OH and R₄ is H;
Formula (III) given above, wherein R₁ is OH, R₂ is OCH₃, R₃ is OH and R₄ is α-OH;
Formula (IV):

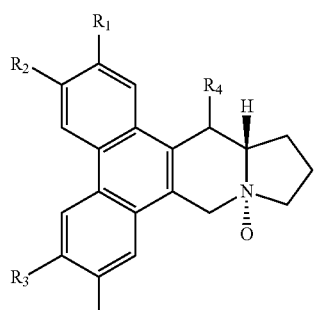

Formula (IV)

wherein R₁ is H, R₂ is OH, R₃ is OH and R₄ is β-OH;
Formula (IV) given above, wherein R₁ is OH, R₂ is OCH₃, R₃ is OCH₃ and R₄ is β-OH;
Formula (IV) given above, wherein R₁ is H, R₂ is OCH₃, R₃ is OCH₃ and R₄ is H; and
Formula (V):

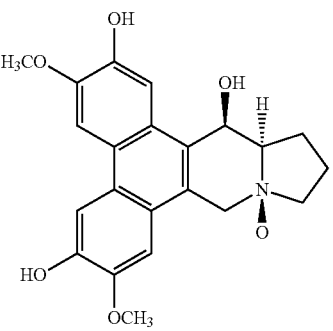

Formula (V)

3. The method of claim 2, wherein phenanthroindolizidine alkaloid has a Formula selected from the group consisting of the following formulas:

a compound having Formula (III), wherein $R_1$ is OH, $R_2$ is $OCH_3$, $R_3$ is OH and $R_4$ is H;
a compound having Formula (III), wherein $R_1$ is OH, $R_2$ is $OCH_3$, $R_3$ is OH and $R_4$ is α-OH;
a compound having Formula (IV), wherein $R_1$ is H, $R_2$ is OH, $R_3$ is OH and $R_4$ is β-OH; and
a compound having Formula (V).

\* \* \* \* \*